United States Patent [19]

Ramsden et al.

[11] 4,442,115
[45] Apr. 10, 1984

[54] 2'HYDROXY TETRAZOLE-5-CARBOXANILIDES AND ANTI-ALLERGIC USE THEREOF

[75] Inventors: Christopher A. Ramsden, Brentwood; Philip Knowles, Rayleigh; Edward J. Lewis, Romford; Edward Lunt, Westcliff-On-Sea; Derek E. Wright, South Benfleet, all of England

[73] Assignee: May & Baker Limited, Essex, England

[21] Appl. No.: 44,511

[22] Filed: Jun. 1, 1979

Related U.S. Application Data

[63] Continuation of Ser. No. 954,785, Oct. 26, 1978, abandoned.

[30] Foreign Application Priority Data

Oct. 28, 1977 [GB] United Kingdom ............... 45097/77

[51] Int. Cl.³ .................... C07D 257/04; A61K 31/41
[52] U.S. Cl. ..................................... 424/269; 548/253
[58] Field of Search ......................... 548/253; 424/269

[56] References Cited

U.S. PATENT DOCUMENTS

| 4,039,672 | 8/1977 | Bulteon et al. | 548/253 |
| 4,069,153 | 6/1978 | Sellstedt | 548/253 |
| 4,146,631 | 3/1979 | Ford et al. | 548/251 |

FOREIGN PATENT DOCUMENTS 842578 12/1976 Belgium .

OTHER PUBLICATIONS

Ettel et al., Coll. of Czech. Chem Comm., vol. 15, pp. 335–339, (1950).

Primary Examiner—Paul M. Coughlan, Jr.
Assistant Examiner—D. B. Springer
Attorney, Agent, or Firm—Stevens, Davis, Miller & Mosher

[57] ABSTRACT

New tetrazole derivatives of the general formula:

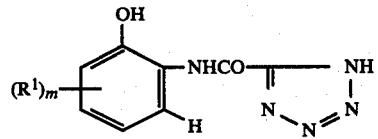

[wherein $R^1$ represents a halogen atom, a straight- or branched-chain alkyl, alkoxy, alkylthio, alkylsulphinyl, alkylsulphonyl or alkylsulphamoyl group, each such group containing from 1 to 6 carbon atoms, a dialkylsulphamoyl, dialkylamino, or dialkylcarbamoyl group (wherein the two alkyl groups may be the same or different and each contains from 1 to 4 carbon atoms), a straight- or branched-chain alkanoyl, alkoxycarbonyl, alkoxycarbonylamino, alkylcarbamoyl or alkanoylamino group containing from 2 to 6 carbon atoms, a cycloalkylcarbonyl group containing from 3 to 8 carbon atoms in the cycloalkyl moiety, or a hydroxy, formyl, nitro, trifluoromethyl, trifluoroacetyl, aryl, benzyloxycarbonylamino, amino, sulphamoyl, cyano, tetrazol-5-yl, carboxy, carbamoyl, benzyloxy, aralkanoyl or aroyl group, or a group of the formula:

$$-CR^2=NOR^3 \qquad II$$

(wherein $R^2$ represents a hydrogen atom or a straight- or branched-chain alkyl group containing from 1 to 5 carbon atoms, an aryl, aralkyl or trifluoromethyl group, or a cycloalkyl group containing from 3 to 8 carbon atoms, and $R^3$ represents a hydrogen atom, or a straight- or branched-chain alkyl group containing from 1 to 6 carbon atoms optionally substituted by a phenyl group, or represents an aryl group optionally substituted by one or more substituents selected from halogen atoms and straight- or branched-chain alkyl and alkoxy groups containing from 1 to 6 carbon atoms and hydroxy, trifluoromethyl and nitro groups), and m represents zero or an integer 1, 2 or 3, the substituents $R^1$ being the same or different when m represents 2 or 3] possess pharmacological properties, in particular properties of value in the treatment of allergic conditions.

43 Claims, No Drawings

2'HYDROXY TETRAZOLE-5-CARBOXANILIDES AND ANTI-ALLERGIC USE THEREOF

This is a continuation of application Ser. No. 954,785 filed Oct. 26, 1978, abandoned.

This invention relates to new therapeutically useful tetrazole derivatives, to processes to their preparation and to pharmaceutical compositions containing them.

As a result of research and experimentation, it has been found that the new tetrazole derivatives of the general formula:

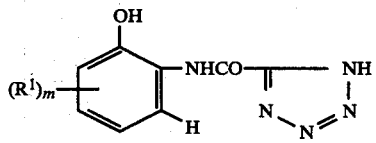

[wherein $R^1$ represents a halogen (i.e. fluorine, chlorine, bromine or iodine) atom, a straight- or branched-chain alkyl, alkoxy, alkylthio, alkylsulphinyl, alkylsulphonyl or alkylsulphamoyl group, each such group containing from 1 to 6 carbon atoms, a dialkylsulphamoyl, dialkylamino, or dialkylcarbamoyl group (wherein the two alkyl groups may be the same or different and each contains from 1 to 4 carbon atoms), a straight- or branched-chain alkanoyl, alkoxycarbonyl, alkoxycarbonylamino, alkylcarbamoyl or alkanoylamino group containing from 2 to 6 carbon atoms, a cycloalkylcarbonyl group containing from 3 to 8 carbon atoms in the cycloalkyl moiety, or a hydroxy, formyl, nitro, trifluoromethyl, trifluoroacetyl, aryl (e.g. phenyl), benzyloxycarbonylamino, amino, sulphamoyl, cyano, tetrazol-5-yl, carboxy, carbamoyl, benzyloxy, aralkanoyl (e.g. phenylacetyl), or aroyl (e.g. benzoyl) group or a group of the formula:

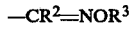

$$-CR^2=NOR^3 \quad II$$

(wherein $R^2$ represents a hydrogen atom or a straight- or branched-chain alkyl group containing from 1 to 5 carbon atoms, an aryl (e.g. phenyl), aralkyl (e.g. benzyl) or trifluoromethyl group, or a cycloalkyl group containing from 3 to 8 carbon atoms, and $R^3$ represents a hydrogen atom, or a straight- or branched-chain alkyl group containing from 1 to 6 carbon atoms optionally substituted by a phenyl group, or represents an aryl (e.g. phenyl) group optionally substituted by one or more substituents selected from halogen atoms and straight- or branched-chain alkyl and alkoxy groups containing from 1 to 6 carbon atoms and hydroxy, trifluoromethyl and nitro groups), and m represents zero or an integer 1, 2 or 3, preferably 1 or 2, the substituents $R^1$ being the same or different when m represents 2 or 3] and pharmaceutically acceptable salts thereof, possess valuable pharmacological properties.

It will be understood by those skilled in the art that each of the hydrogen atoms depicted in general formula I in the moieties OH, NHCO and NH may give rise to tautomerism and that all the resulting tautomeric forms may be present to a greater or lesser degree and are in a state of dynamic equilibrium with each other. Furthermore the substituents $R^1$, $R^2$ and $R^3$ may contain chiral centres and thus give rise to optical isomerism and the group of formula II may be in the syn or anti configuration. The present invention embraces all optical and geometrical isomers of general formula I and all tautomers of compounds of general formula I and mixtures thereof.

The present invention includes pharmaceutically acceptable salts of compounds of formula I with pharmaceutically acceptable bases. By the term "pharmaceutically acceptable salts" is meant salts the cations of which are relatively innocuous to the animal organism when used in therapeutic doses so that the beneficial pharmacological properties of the parent compounds of general formula I are not vitiated by side effects ascribable to those cations. Suitable salts include the alkali metal, e.g. sodium and potassium, and ammonium salts and salts of amines known in the art to be pharmaceutically acceptable, e.g. ethylene diamine, choline, diethanolamine, triethanolamine, octadecylamine, diethylamine, triethylamine, 2-amino-2-(hydroxymethyl)propane-1,3-diol and 1-(3,4-dihydroxyphenyl)-2-isopropylaminoethanol.

Pharmaceutically acceptable salts may be prepared by the reaction together of a compound of formula I and the appropriate base, for example at an elevated temperature, with or without an appropriate solvent, preferably followed by recrystallisation from an appropriate solvent, for example a hydroxylic solvent (e.g. water) of the salt so formed.

In this specification when reference is made to compounds of formula I reference is also intended to their pharmaceutically acceptable salts, where the context so permits.

The tetrazole derivatives of the present invention possess valuable pharmacological properties, in particular properties of value in the treatment of allergic conditions, for example respiratory disorders such as those manifested by the interaction of tissue-fixed antibodies with specific antigens, such as allergic bronchial asthma.

A class of compounds of general formula I which is important includes those compounds wherein $R^1$ represents a halogen atom or a straight- or branched-chain alkyl, alkoxy, or alkylsulphonyl group, each such group containing from 1 to 4 carbon atoms, a dialkylcarbamoyl group (wherein the two alkyl groups may be the same or different and each contains 1 or 2 carbon atoms), a straight- or branched-chain alkanoyl, alkoxycarbonyl, or alkanoylamino group containing from 2 to 4 carbon atoms, a cycloalkylcarbonyl group containing from 3 to 6 carbon atoms in the cycloalkyl moiety, or a nitro, trifluoroacetyl, amino, cyano or phenylacetyl group or a group of formula II (wherein $R^2$ represents a straight- or branched-chain alkyl group containing from 1 to 3 carbon atoms, and $R^3$ represents a hydrogen atom or a straight- or branched-chain alkyl group containing from 1 to 3 carbon atoms), and m represents zero or an integer 1 or 2, the substituents $R^1$ being the same or different when m represents 2, and their pharmaceutically acceptable salts.

Especially important are those compounds of general formula I wherein $R^1$ represents a fluorine or bromine atom or a methyl, ethyl, propyl, methoxy, methylsulphonyl, dimethylcarbamoyl, acetyl, propionyl, butyryl, isobutyryl, methoxycarbonyl, ethoxycarbonyl, acetylamino, cyclopropylcarbonyl, nitro, trifluoroacetyl, amino, cyano, phenylacetyl, 1-(hydroxyimino)ethyl or 1-(methoxyiminoethyl) group, and m represents zero or an integer 1 or 2, the substituents $R^1$ being the same or different when m represents 2, and their pharmaceutically acceptable salts.

The class of compounds of general formula I wherein the benzene ring carries at least one substituent $R^1$ and $R^1$ represents a straight- or branched-chain alkoxy group containing from 1 to 4 carbon atoms or a straight- or branched-chain alkanoyl or alkoxycarbonyl group containing from 2 to 4 carbon atoms, or a group of formula II (wherein $R^2$ and $R^3$ are as hereinbefore defined), preferably in the 3-position of the benzene ring, any other substituents $R^1$ present being as hereinbefore defined, and their pharmaceutically acceptable salts, are of great importance.

Compounds of general formula I wherein the benzene ring carries at least one substituent $R^1$ and $R^1$ represents an alkanoyl group containing from 2 to 4 carbon atoms, preferably in the 3-position of the benzene ring, any other substituents $R^1$ present being as hereinbefore defined, and their pharmaceutically acceptable salts, are of outstanding importance.

Individual compounds of formula I of particular importance include the following:

| Compound | Code |
|---|---|
| 2'-hydroxytetrazole-5-carboxanilide; | A |
| 3'-acetyl-2'-hydroxy-5'-methyltetrazole-5-carboxanilide; | B |
| 3'-ethyl-2'-hydroxytetrazole-5-carboxanilide; | C |
| 3'-acetyl-5'-ethyl-2'-hydroxytetrazole-5-carboxanilide; | D |
| 3'-acetyl-2'-hydroxy-5'-nitrotetrazole-5-carboxanilide; | E |
| 3'-acetyl-5'-acetylamino-2'-hydroxytetrazole-5-carboxanilide; | F |
| 2'-hydroxy-3'-isobutyryl-5'-methyltetrazole-5-carboxanilide; | G |
| 3'-acetyl-5'-cyano-2'-hydroxytetrazole-5-carboxanilide; | H |
| 3'-cyclopropylcarbonyl-2'-hydroxy-5'-methyltetrazole-5-carboxanilide; | I |
| 2'-hydroxy-5'-methyl-3'-trifluoroacetyltetrazole-5-carboxanilide; | J |
| 3'-acetyl-5'-fluoro-2'-hydroxytetrazole-5-carboxanilide; | K |
| 3'-acetyl-5'-bromo-2'-hydroxytetrazole-5-carboxanilide; | L |
| 3'-acetyl-2'-hydroxy-5'-methoxytetrazole-5-carboxanilide; | M |
| 5'-cyano-2'-hydroxy-3'-propionyltetrazole-5-carboxanilide; | N |
| 2'-hydroxy-5'-methyl-3'-phenylacetyltetrazole-5-carboxanilide; | O |
| 3'-acetyl-5'-amino-2'-hydroxytetrazole-5-carboxanilide; | P |
| 3'-acetyl-2'-hydroxy-5'-methylsulphonyltetrazole-5-carboxanilide; | Q |
| 2'-hydroxy-3'-methoxytetrazole-5-carboxanilide; | R |
| 5'-ethyl-2'-hydroxy-3'-methoxytetrazole-5-carboxanilide; | S |
| 2'-hydroxy-3'-methoxy-5'-methyltetrazole-5-carboxanilide; | T |
| 3'-butyryl-2'-hydroxy-5'-methyltetrazole-5-carboxanilide; | U |
| 3'-(N,N—dimethylcarbamoyl)-2'-hydroxy-5'-methyltetrazole-5-carboxanilide; | V |
| 2'-hydroxy-3'-methoxycarbonyl-5'-methyltetrazole-5-carboxanilide; | W |
| 3'-ethoxycarbonyl-2'-hydroxy-5'-methyltetrazole-5-carboxanilide; | X |
| 3'-acetyl-2'-hydroxy-5'-propyltetrazole-5-carboxanilide; | Y |
| 3'-acetyl-2'-hydroxytetrazole-5-carboxanilide; | Z |
| 5'-ethyl-2'-hydroxy-3'-propionyltetrazole-5-carboxanilide; | AA |
| 2'-hydroxy-5'-methyl-3'-propionyltetrazole-5-carboxanilide; | BB |
| 5'-bromo-2'-hydroxy-3'-methoxytetrazole-5-carboxanilide; | CC |
| 2'-hydroxy-3'-(1-hydroxyimino)ethyl-5'-methyltetrazole-5-carboxanilide; | DD |
| 2'-hydroxy-3'-(1-methoxyimino)ethyl-5'-methyltetrazole-5-carboxanilide; | EE |
| 5'-ethyl-2'-hydroxy-3'-(1-hydroxyimino)ethyltetrazole-5-carboxanilide; and | FF |
| 5'-ethyl-2'-hydroxy-3'-(1-methoxyimino)ethyltetrazole-5-carboxanilide; | GG | and their pharmaceutically acceptable salts.

The letters A to GG are assigned to the compounds for easy reference later in the specification, for example in the following Tables. The presently preferred compound is that identified as D.

In pharmacological tests the new compounds suppress the passive cutaneous anaphylactic (PCA) reaction resulting from combination of tissue-fixed reaginic antibodies with the appropriate antigenic material (termed reagin-allergen combination) and carried out in an essentially similar manner to that described by Ogilvie [Nature (Lond.), (1964), 204, 91–92; Immunology, (1967), 12, 112–131]. In the method used to test these compounds sera were obtained from rats which had been infected with larvae of the nematode parasite *Nippostrongylus brasiliensis;* as a result of the parasitic infestation reaginic antibodies are elaborated in the host mammal and are found in sera removed from such animals. Other, non-infected, rats received intradermal injections of appropriate dilutions of such sera and were then given the allergenic material along with Evans' blue dye intravenously forty-eight hours later.

The allergenic material consisted of supernatant fluid after centrifugation of homogenates of adult *Nippostrongylus brasiliensis* worms which had been macerated in Tyrode's solution. The sites of PCA reactions were visualised by the effusion of Evans' blue dye from the circulation into those areas as a result of increased capillary permeability caused by the release of biologically-active substances from cells where reagin-allergen combination had occurred. The new compounds when given intravenously to the rats just before injection of allergen, or administered orally thirty minutes before intravenous injection of allergen, were able to prevent the development of the PCA reaction, as shown below in Table I and Table II.

Table I shows the intravenous dose, expressed in mg/kg animal body weight, which produces 100% inhibition of the PCA reaction (ED 100).

Table II shows the oral dose, expressed in mg/kg animal body weight, which produces 50% inhibition of the PCA reaction (ED 50).

TABLE I

| Compound | | | | | | | |
|---|---|---|---|---|---|---|---|
| | A | B | C | D | E | G | |
| ED 100 (i.v.) | 0.2 | 0.01 | 0.1 | 0.01 | 0.02 | 0.02 | |
| | H | I | K | L | M | N | P |
| ED 100 (i.v.) | 0.01 | 0.02 | 0.01 | 0.05 | 0.01 | 0.02 | 0.05 |
| | R | S | T | U | V | W | X |
| ED 100 (i.v.) | 0.02 | 0.01 | 0.02 | 0.05 | 0.2 | 0.05 | 0.01 |
| | Y | Z | AA | BB | CC | DD | EE |
| ED 100 (i.v.) | 0.01 | 0.005 | 0.01 | 0.02 | 0.05 | 0.002 | 0.02 |

TABLE II

| Compound | | | | | | | |
|---|---|---|---|---|---|---|---|
| | A | B | C | D | E | G | H |
| ED 50 (p.o.) | 5.5 | 0.06 | 0.7 | 0.19 | 0.04 | 3.2 | 0.4 |
| | R | S | T | W | X | Y | Z |
| ED 50 (p.o.) | 2.9 | 1.8 | 6.5 | 5.6 | 36 | 0.46 | 0.06 |

TABLE II-continued

| Compound | AA | BB | CC |
|---|---|---|---|
| ED 50 (p.o.) | 1.3 | 0.88 | 16 |

The utility of the compounds of formula I is enhanced by the fact that they are only of very low toxicity to mammals.

For example, compounds B and I were administered orally to mice at a rate of 1000 mg/kg animal body weight, and no deaths occurred during the following observation period of 3 days even at this enormous dose.

Compounds of formula I may be prepared by the application or adaptation of known methods, for example methods as described hereinafter.

By the term "known methods", as used in this specification, is meant methods heretofore used for described in the literature.

Thus, according to a feature of the present invention, compounds of general formula I, except those wherein $R^1$ represents a group of formula II, are prepared by the replacement by hydrogen atoms of the protecting groups in compounds of the general formula:

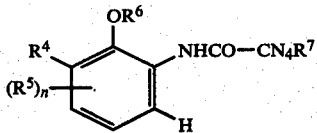

III

[wherein $R^4$ represents a hydrogen or halogen atom, a straight- or branched-chain alkyl, alkoxy, alkylthio, alkylsulphinyl, alkylsulphonyl or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl, alkoxycarbonyl, alkoxycarbonylamino, alkylcarbamoyl or alkanoylamino group containing from 2 to 6 carbon atoms, a cycloalkylcarbonyl group containing from 3 to 8 carbon atoms in the cycloalkyl moiety, or a formyl, nitro, trifluoromethyl, trifluoroacetyl, aryl (e.g. phenyl), benzyloxycarbonylamino, amino, sulphamoyl, cyano, tetrazol-5-yl, carboxy, carbamoyl, benzyloxy, aralkanoyl (e.g. phenylacetyl), or aroyl (e.g. benzoyl) group, $R^5$ represents a halogen atom or a straight- or branched-chain alkyl, alkoxy, alkylthio, alkylsulphinyl, alkylsulphonyl, or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl, alkoxycarbonyl, alkoxycarbonylamino, alkylcarbamoyl or alkanoylamino group containing from 2 to 6 carbon atoms, a cycloalkylcarbonyl group containing from 3 to 8 carbon atoms in the cycloalkyl moiety, or a formyl, nitro, trifluoromethyl, trifluoroacetyl, aryl (e.g. phenyl), benzyloxycarbonylamino, amino, sulphamoyl, cyano, tetrazol-5-yl, carboxy, carbamoyl, benzyloxy, aralkanoyl (e.g. phenylacetyl), or aroyl (e.g. benzoyl) group, and n represents zero or an integer 1 or 2, the substituents $R^5$ being the same or different when n represents 2, $R^6$ represents a protecting group, for example a benzyl group, or, when $R^4$ represents a straight- or branched-chain alkylsulphonyl or alkylsulphamoyl group, each such group containing from 1 to 6 carbon atoms, a dialkylsulphamoyl or dialkylcarbamoyl group (wherein the two alkyl groups may be the same or different and each contains from 1 to 4 carbon atoms), a straight- or branched-chain alkanoyl, alkoxycarbonyl or alkylcarbamoyl group containing from 2 to 6 carbon atoms, a cycloalkylcarbonyl group containing from 3 to 8 carbon atoms in the cycloalkyl moiety, or a formyl, trifluoroacetyl, sulphamoyl, carboxy, carbamoyl, aralkanoyl (e.g. phenylacetyl), or aroyl (e.g. benzoyl) group, $R^6$ may alternatively represent a hydrogen atom, $CN_4$ signifies a tetrazol-5-yl group and $R^7$ represents a protecting group, preferably a benzyl group or a 4-methoxybenzyl group, either in the 1-position or in the 2-position of said tetrazol-5-yl group, or a mixture of such isomers].

The conversion of compounds of formula III to compounds of formula I is carried out by the conversion of the various protecting groups present to hydrogen atoms, in any order, by appropriately selecting the reaction conditions.

For example, (a) benzyl groups within the definition of $R^6$ or $R^7$ and 4-methoxybenzyl groups within the definition of $R^7$ are replaced by hydrogen atoms by reduction, generally by means of hydrogenation in the presence of a catalyst such as platinum or palladium on charcoal in an organic solvent, for example N-methyl-pyrrolid-2-one, ethanol or acetic acid; or (b) benzyl groups within the definition of $R^6$ are replaced by hydrogen atoms and, incidentally, any benzyloxycarbonylamino groups present within the definition of $R^4$ or $R^5$ may be converted into amino groups, by the action of acetic acid and hydrogen bromide; or (c) 4-methoxybenzyl groups within the definition of $R^7$ are replaced by hydrogen atoms by reaction with an acid, such as trifluoroacetic acid, optionally at an elevated temperature; or (d) benzyl and 4-methoxybenzyl groups within the definition of $R^6$ or $R^7$ are replaced by hydrogen atoms by the action of anhydrous aluminium chloride, preferably in an organic solvent, for example dichloromethane, preferably at an elevated temperature, e.g. the reflux temperature of the reaction mixture, preferably followed by reaction of the resulting mixture with aqueous hydrochloric acid at a temperature between 0° and 100° C.

Sometimes, during the conversion of the protecting groups present to hydrogen atoms, there is a concomitant interconversion of other groups, represented by symbols $R^4$ and $R^5$. For example, acetyl groups are occasionally reduced to form ethyl groups during the conversion of benzyl groups, within the definition of $R^6$ or $R^7$, to hydrogen atoms by catalytic hydrogenation, and benzyloxy groups may be converted to hydroxy groups.

According to a further feature of the invention, compounds of formula I (except those wherein $R^1$ represents an alkylsulphinyl, alkoxycarbonylamino, alkanoylamino, hydroxy, benzyloxycarbonylamino, amino, cyano, carboxy, carbamoyl or benzyloxy group or a group of formula II) are prepared by the reaction of compounds of the general formula:

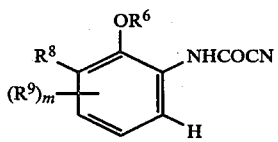

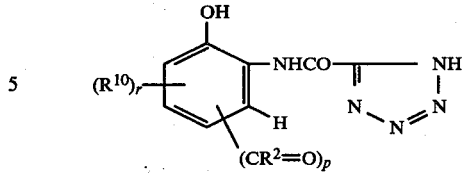

[wherein $R^8$ represents a hydrogen or halogen atom, a straight- or branched-chain alkyl, alkoxy, alkylthio, alkylsulphonyl or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl, alkoxycarbonyl or alkylcarbamoyl group containing from 2 to 6 carbon atoms, a cycloalkylcarbonyl group containing from 3 to 8 carbon atoms in the cycloalkyl moiety, or a formyl, nitro, trifluoromethyl, trifluoroacetyl, aryl (e.g. phenyl), sulphamoyl, tetrazol-5-yl, aralkanoyl (e.g. phenylacetyl), or aroyl (e.g. benzoyl) group, $R^9$ represents a halogen atom or a straight- or branched-chain alkyl, alkoxy, alkylthio, alkylsulphonyl, or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl, alkoxycarbonyl or alkylcarbamoyl group containing from 2 to 6 carbon atoms, a cycloalkylcarbonyl group containing from 3 to 8 carbon atoms in the cycloalkyl moiety, or a formyl, nitro, trifluoromethyl, trifluoroacetyl, aryl (e.g. phenyl), sulphamoyl, tetrazol-5-yl, aralkanoyl (e.g. phenylacetyl), or aroyl (e.g. benzoyl) group, and m represents zero or an integer 1 or 2, the substituents $R^9$ being the same or different when m represents 2, $R^6$ represents a protecting group, for example a benzyl group, or, when $R^8$ represents a straight- or branched-chain alkanoyl, alkoxycarbonyl or alkylcarbamoyl group containing from 2 to 6 carbon atoms, a cycloalkylcarbonyl group containing from 3 to 8 carbon atoms in the cycloalkyl moiety, or a formyl, trifluoroacetyl, sulphamoyl, aralkanoyl (e.g. phenylacetyl), or aroyl (e.g. benzoyl) group, $R^6$ may alternatively represent a hydrogen atom] with hydrazoic acid or a salt thereof, for example sodium azide or potassium azide, preferably in the presence of an aluminium salt, e.g. aluminium chloride, preferably in an organic solvent, e.g. tetrahydrofuran, and preferably at an elevated temperature, for example the reflux temperature of the reaction mixture, if necessary followed or accompanied by conversion of the protecting group represented by $R^6$ to a hydrogen atom, under the conditions of the reaction of the compound of formula IV with the hydrazoic acid or salt thereof.

According to a further feature of the present invention, compounds of formula I wherein at least one group $R^1$ represents a group of formula II (wherein $R^2$ and $R^3$ are as hereinbefore defined), any other groups $R^1$ present being as hereinbefore defined (except those wherein $R^1$ represents an alkanoyl, alkoxycarbonyl, cycloalkylcarbonyl, formyl, trifluoroacetyl, cyano, aralkanoyl or aroyl group) are prepared from compounds of the general formula:

[wherein $R^{10}$ represents a halogen atom, a straight- or branched-chain alkyl, alkoxy, alkylthio, alkylsulphinyl, alkylsulphonyl or alkylsulphamoyl group, each such group containing from 1 to 6 carbon atoms, a dialkylsulphamoyl, dialkylamine or dialkylcarbamoyl group (wherein the two alkyl groups may be the same or different and each contains from 1 to 4 carbon atoms), a straight- or branched-chain alkoxycarbonylamino, alkylcarbamoyl or alkanoylamino group containing from 2 to 6 carbon atoms, or a hydroxy, nitro, trifluoromethyl, aryl (e.g. phenyl), benzyloxycarbonylamino, amino, sulphamoyl, tetrazol-5-yl, carboxy, carbamoyl or benzyloxy group, $R^2$ is as hereinbefore defined, p represents an integer 1, 2 or 3, and r represents zero or an integer 1 or 2, the substituents $R^{10}$ being the same or different when r represents 2, and the sum of p and r is 1, 2 or 3] within general formula I, by the application or adaptation of known methods for the preparation of oximes from aldehydes and ketones, for example by reaction with compounds of the general formula:

$$H_2NOR^3 \qquad VI$$

(wherein $R^3$ is as hereinbefore defined) in the form of a salt, e.g. the hydrochloride, thereof.

Generally the reaction is carried out in the presence of a base, for example the hydroxide, carbonate or bicarbonate of an alkali metal, e.g. sodium hydroxide, sodium carbonate, or sodium bicarbonate, in a polar medium such as N-methylpyrrolid-2-one, and at a temperature near or above the ambient temperature, e.g. between 15° and 100° C.

As a further feature of the invention, compounds of the general formula:

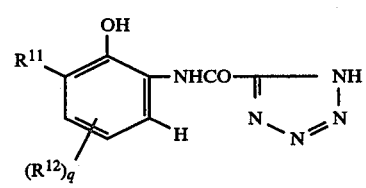

[wherein $R^{11}$ represents a straight- or branched-chain alkylsulphonyl or alkylsulphamoyl group, each such group containing from 1 to 6 carbon atoms, a dialkylsulphamoyl or dialkylcarbamoyl group (wherein the two alkyl groups may be the same or different and each contains from 1 to 4 carbon atoms), a straight- or branched-chain alkanoyl, alkoxycarbonyl or alkylcarbamoyl group containing from 2 to 6 carbon atoms, a cycloalkylcarbonyl group containing from 3 to 8 carbon atoms in the cycloalkyl moiety, or a formyl, trifluoroacetyl, sulphamoyl, cyano, carbamoyl, aralkanoyl (e.g. phenylacetyl), or aroyl (e.g. benzoyl) group, $R^{12}$ represents a halogen atom or a straight- or branched-chain alkyl, alkoxy, alkylthio, alkylsulphonyl, or alkylsulphamoyl group, each such group containing from 1 to 6 carbon atoms, a dialkylsulphamoyl, dialkylamino or dialkylcarbamoyl group (wherein the two alkyl groups may be the same or different and each contains from 1 to 4 carbon atoms), a straight- or branched-chain alkanoyl, alkoxycarbonyl, alkoxycarbonylamino, alkylcarbamoyl or alkanoylamino group containing from 2 to 6 carbon atoms, a cycloalkylcarbonyl group containing from 3 to 8 carbon atoms in the cycloalkyl moiety, or a formyl, nitro, trifluoromethyl, trifluoroacetyl, aryl (e.g. phenyl), benzyloxycarbonylamino, sulphamoyl, cyano, tetrazol-5-yl, carbamoyl, benzyloxy, aralkanoyl (e.g. phenylacetyl), or aroyl (e.g. benzoyl) group, or a group of formula II (wherein $R^2$ and $R^3$ are as hereinbefore defined) and q represents zero or an integer 1 or 2, the substituents $R^{12}$ being the same or different when n represents 2] within general formula I are prepared by the reaction of a compound of the general formula:

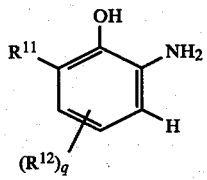

VIII (wherein $R^{11}$, $R^{12}$ and q are as hereinbefore defined) with the dipotassium salt of tetrazole-5-carboxylic acid, in the presence of N,N-dimethyl(chloromethyleneimmonium) chloride or a source thereof (for example a mixture of dimethylformamide and an acid chloride such as oxalyl chloride), preferably near or below room temperature, e.g. between $-25°$ and $+35°$ C.

Compounds of formulae III, IV, V, VI and VIII may be prepared by the application or adaptation of known methods, for example methods as hereinafter described in the following Examples and Reference Examples.

The following Examples illustrate the preparation of the new compounds of the present invention.

The Reference Examples following thereafter illustrate the preparation of starting materials used in the Examples.

EXAMPLE 1

Compound A

A solution of 1-benzyl-2'-benzyloxy-1H-tetrazole-5-carboxanilide (2.0 g) in glacial acetic acid (100 ml) was hydrogenated at 53° C. and 4.1 kg/cm² for 18.5 hours, using a catalyst of palladium on charcoal (5% w/w). The mixture was filtered and the filtrate was evaporated at 40° C. in vacuo. The resulting solid was dissolved in a minimum volume of aqueous ammonia solution (2 N). The solution was filtered and then acidified with dilute hydrochloric acid (2 N). The resulting solid was filtered off, dried and recrystallised from aqueous dimethylformamide to give 2'-hydroxytetrazole-5-carboxanilide (0.45 g), m.p. 220°–223° C.

EXAMPLE 2

Compound B

A solution of 3'-acetyl-1-benzyl-2'-hydroxy-5'-methyl-1H-tetrazole-5-carboxanilide (1.6 g) in glacial acetic acid (73 ml) was hydrogenated at 55° C. and 4.1 kg/cm² for 12 hours, using a catalyst of palladium on charcoal (5% w/w). The mixture was filtered and the filtrate was evaporated in vacuo to give a solid residue, which was purified by chromatography on a column of silica gel, using a mixture of chloroform, methanol and formic acid (86:10:4 by volume) is eluant. The fastest moving fraction (pale yellow) was collected and further purified by thin layer chromatography on silica gel, using a mixture of chloroform, methanol and formic acid (86:10:4 by volume) as eluant, and the product was recrystallised from aqueous dimethylformamide to give 3'-acetyl-2'-hydroxy-5'-methyltetrazole-5-carboxanilide (0.2 g), m.p. 245°–247° C. (with decomposition).

EXAMPLE 3

Compound C

A solution of 3'-acetyl-1-benzyl-2'-hydroxy-1H-tetrazole-5-carboxanilide (2.6 g) in glacial acetic acid (100 ml) was hydrogenated at 52° C. and 4.1 kg/cm² for 6 hours, using a catalyst of palladium on charcoal (5% w/w). The mixture was filtered and the filtrate was evaporated in vacuo to give a solid residue, which was recrystallised by dissolving in hot dimethylformamide (7 ml) and slowly adding a large volume of water (100 ml). The colourless solid which crystallised out was collected and discarded as an unwanted by-product. The mother liquor was evaporated under diminished pressure, and the resulting residue was recrystallised from a small volume of aqueous dimethylformamide to give 3'-ethyl-2'-hydroxytetrazole-5-carboxanilide (0.3 g) in the form of pale cream crystals, m.p. 185°–187° C.

EXAMPLE 4

Compounds D,B,E,F,G,H,I,J,K,L,M,N,O,P and Q

A solution of 3'-acetyl-5'-ethyl-2'-hydroxy-1-(4-methoxybenzyl)-1H-tetrazole 5-carboxanilide (10.0 g) and methoxybenzene (10.0 g) in trifluoroacetic acid (150 ml) was heated at reflux for 45 minutes, and then the solvent was removed in vacuo. The residue was stirred with diethyl ether (100 ml) for 20 minutes, and the precipitated solid was filtered off and recrystallised from a mixture of dimethylformamide and water to give 3'-acetyl-5'-ethyl-2'-hydroxytetrazole-5-carboxanilide (6.5 g), m.p. 239°–242° C. (with decomposition).

By replacing the 3'-acetyl-5'-ethyl-2'-hydroxy-1-(4-methoxybenzyl)-1H-tetrazole-5-carboxanilide, used as starting material, by 3'-acetyl-5'-ethyl-2'-hydroxy-2-(4-methoxybenzyl)-2H-tetrazole-5-carboxanilide, the same product was obtained.

By proceeding in a similar manner, but replacing the 3'-acetyl-5'-ethyl-2'-hydroxy-1-(4-methoxybenzyl)-1H-tetrazole-5-carboxanilide used as starting material by the appropriate quantities of 3'-acetyl-2'-hydroxy-1-(4-methoxybenzyl)-5'-methyl-1H-tetrazole-5-carboxanilide;

3'-acetyl-2'-hydroxy-1-(4-methoxybenzyl)-5'-nitro-1H-tetrazole-5-carboxanilide;

3'-acetyl-5'-acetylamino-2'-hydroxy-1-(4-methoxybenzyl)-1H-tetrazole-5-carboxanilide;

2'-hydroxy-3'-isobutyryl-1-(4-methoxybenzyl)-5'-methyl-1H-tetrazole-5-carboxanilide;

3'-acetyl-5'-cyano-2'-hydroxy-1-(4-methoxybenzyl)-1H-tetrazole-5-carboxanilide;

3'-cyclopropylcarbonyl-2'-hydroxy-1-(4-methoxybenzyl)-5'-methyl-1H-tetrazole-5-carboxanilide;

2'-hydroxy-1-(4-methoxybenzyl)-5'-methyl-3'-trifluoroacetyl-1H-tetrazole-5-carboxanilide;

3'-acetyl-5'-fluoro-2'-hydroxy-1-(4-methoxybenzyl)-1H-tetrazole-5-carboxanilide;

3'-acetyl-5'-bromo-2'-hydroxy-1H-tetrazole-5-carboxanilide;

3'-acetyl-2'-hydroxy-5'-methoxy-1-(4-methoxybenzyl)-1H-tetrazole-5-carboxanilide;

5'-cyano-2'-hydroxy-1-(4-methoxybenzyl)-3'-propionyl-1H-tetrazole-5-carboxanilide;

2'-hydroxy-1-(4-methoxybenzyl)-5'-methyl-3'-phenylacetyl-1H-tetrazole-5-carboxanilide;

3'-acetyl-5'-amino-2'-hydroxy-1-(4-methoxybenzyl)-1H-tetrazole-5-carboxanilide hydrochloride; and 3'-acetyl-2'-hydroxy-1-(4-methoxybenzyl)-5'-methylsulphonyl-1H-tetrazole-5-carboxanilide; respectively, there were prepared:

3'-acetyl-2'-hydroxy-5'-methyltetrazole-5-carboxanilide, m.p. 257° C. (with decomposition) (recrystallised from a mixture of dimethylformamide and water);

3'-acetyl-2'-hydroxy-5'-nitrotetrazole-5-carboxanilide, m.p. 239°–240° C. (with decomposition) (recrystallised from a mixture of dimethylformamide and water);

3'-acetyl-5'-acetylamino-2'-hydroxytetrazole-5-carboxanilide, m.p. 270°–271° C. (with decomposition) (recrystallised from a mixture of dimethylformamide and water);

2'-hydroxy-3'-isobutyryl-5'-methyltetrazole-5-carboxanilide, m.p. 224°–225° C. (with decomposition) (recrystallised from a mixture of methanol and water);

3'-acetyl-5'-cyano-2'-hydroxytetrazole-5-carboxanilide, m.p. 270°–274° C. (with decomposition) (recrystallised from a mixture of dimethylformamide and water);

3'-cyclopropylcarbonyl-2'-hydroxy-5'-methyltetrazole-5-carboxanilide, m.p. 261°–263° C. (with decomposition) (recrystallised from a mixture of dimethylformamide and water);

2'-hydroxy-5'-methyl-3'-trifluoroacetyltetrazole-5-carboxanilide, m.p. 248°–249° C. (with decomposition) (recrystallised from nitromethane);

3'-acetyl-5'-fluoro-2'-hydroxytetrazole-5-carboxanilide, m.p. 237°–239° C. (with decomposition) (recrystallised from a mixture of dimethylformamide and water);

3'-acetyl-5'-bromo-2'-hydroxytetrazole-5-carboxanilide, m.p. 252°–254° C. (with decomposition) (recrystallised from a mixture of dimethylformamide and water);

3'-acetyl-2'-hydroxy-5'-methoxytetrazole-5-carboxanilide, m.p. 251°–253° C. (with decomposition) (recrystallised from a mixture of dimethylformamide and water);

5'-cyano-2'-hydroxy-3'-propionyltetrazole-5-carboxanilide, m.p. 257°–259° C. (with decomposition) (recrystallised from a mixture of dimethylformamide and water);

2'-hydroxy-5'-methyl-3'-phenylacetyltetrazole-5-carboxanilide, m.p. 202° C. (with decomposition) (recrystallised from ethanol);

3'-acetyl-5'-amino-2'-hydroxytetrazole-5-carboxanilide hydrochloride, m.p. greater than 360° C. (This product was purified by dissolving it in a solution of hydrogen chloride in ethanol (5 N), stirring for 20 minutes and removing the solvent at 25° C. in vacuo. This process was repeated several times and then finally the residue was washed with diethyl ether); and 3'-acetyl-2'-hydroxy-5'-methylsulphonyltetrazole-5-carboxanilide, m.p. 256°–259° C. (with decomposition) (recrystallised from a mixture of dimethylformamide and water).

EXAMPLE 5

Compounds R, S and T

By proceeding in a manner similar to that described in Example 1, but replacing the 1-benzyl-2'-benzyloxy-1H-tetrazole-5-carboxanilide used as starting material by the appropriate quantities of 1-benzyl-2'-benzyloxy-3'-methoxy-1H-tetrazole-5-carboxanilide;

1-benzyl-2'-benzyloxy-5'-ethyl-3'-methoxy-1H-tetrazole-5-carboxanilide; and 1-benzyl-2'-benzyloxy-3'-methoxy-5'-methyl-1H-tetrazole-5-carboxanilide, respectively, there were prepared:

2'-hydroxy-3'-methoxytetrazole-5-carboxanilide, m.p. 218°–220° C. (with decomposition) (recrystallised from water);

5'-ethyl-2'-hydroxy-3'-methoxytetrazole-5-carboxanilide, m.p. 233°–235° C. (with decomposition) (recrystallised from glacial acetic acid); and 2'-hydroxy-3'-methoxy-5'-methyltetrazole-5-carboxanilide, m.p. 220°–222° C.

EXAMPLE 6

Compounds U and V

A stirred solution of 1-benzyl-3'-butyryl-2'-hydroxy-5'-methyl-1H-tetrazole-5-carboxanilide in dichloromethane (75 ml), heated at reflux, was treated with anhydrous aluminium chloride (2.2 g) over a period of 15 minutes. After heating and stirring for a further hour, the mixture was cooled and treated with aqueous hydrochloric acid (2 N; 50 ml). The resulting suspension was heated at reflux with stirring for 15 minutes and then cooled. The precipitated solid was filtered off and combined with a residue which was subsequently obtained by evaporation of the dichloromethane layer of the filtrate. This combined solid was digested in aqueous sodium carbonate solution (2 N) at 90° C., then filtered to remove insoluble material and acidified by treatment with concentrated hydrochloric acid. Recrystallisation from a mixture of dimethylformamide and water gave 3'-butyryl-2'-hydroxy-5'-methyltetrazole-5-carboxanilide (0.78 g), m.p. 231°–233° C. (with decomposition).

By proceeding in a similar manner, but replacing the 1-benzyl-3'-butyryl-2'-hydroxy-5'-methyl-1H-tetrazole-5-carboxanilide, used as starting material, by the appropriate quantity of 1-benzyl-3'-(N,N-dimethylcarbamoyl)-2'-hydroxy-5'-methyl-1H-tetrazole-5-carboxanilide, there was prepared 3'-(N,N-dimethylcarbamoyl)-2'-hydroxy-5'-methyltetrazole-5-carboxanilide, m.p. 235° C. (with decomposition) (recrystallised from nitromethane).

EXAMPLE 7

Compounds W and X

1-Benzyl-2'-hydroxy-3'-methoxycarbonyl-5'-methyl-1H-tetrazole-5-carboxanilide (3.0 g) was added, with stirring, to a suspension of anhydrous aluminium chloride (3.6 g) in dichloromethane (150 ml). After stirring and heating at reflux for 150 minutes, the mixture was poured into a mixture of ice (100 g), aqueous hydrochloric acid (2 N; 100 ml) and ethyl acetate (100 ml), and stirring was continued for a further period of 2 hours. The remaining insoluble material was filtered off and the organic layer was washed with water (3×20 ml) and dried over anhydrous sodium sulphate. Evaporation of the solvent gave a yellow solid, which was then digested in aqueous potassium bicarbonate solution (5% w/v; 100 ml), and the resulting solution was treated with charcoal and filtered. Acidification of the filtrate gave a solid, which was recrystallised from nitromethane to give 2'-hydroxy-3'-methoxycarbonyl-5'-methyltetrazole-5-carboxanilide (1.2 g), m.p. 238°–240° C.

By proceeding in a similar manner, but replacing the 1-benzyl-2'-hydroxy-3'-methoxycarbonyl-5'-methyl-1H-tetrazole-5-carboxanilide, used as starting material, by the appropriate quantity of 1-benzyl-3'-ethoxycarbonyl-2'-hydroxy-5'-methyl-1H-tetrazole-5-carboxanilide, there was prepared 3'-ethoxycarbonyl-2'-hydroxy-5'-methyltetrazole-5-carboxanilide, m.p. 252°–254° C. (with decomposition).

EXAMPLE 8

Compound D

A mixture of 3'-acetyl-5'-ethyl-2'-hydroxy-1-(4-methoxybenzyl)-1H-tetrazole-5-carboxanilide (0.41 g), trifluoroacetic acid (15 ml) and methoxybenzene (1.0 g) was heated at reflux for 45 minutes. The mixture was then cooled, and the solvents were removed under reduced pressure. The residue was treated with aqueous ammonia (2 N; 10 ml), washed with diethyl ether (10 ml), and the aqueous layer was separated off, cooled in an ice-bath and acidified by treatment with concentrated hydrochloric acid. The resulting solid was filtered off to give 3'-acetyl-5'-ethyl-2'-hydroxytetrazole-5-carboxanilide (30 mg), m.p. 238°–240° C. (with decomposition).

EXAMPLE 9

Compound D

By proceeding in a manner similar to that hereinbefore described in Example 1, but replacing the 1-benzyl-2'-benzyloxy-1H-tetrazole-5-carboxanilide used as a starting material by the appropriate quantity of 3'-acetyl-2-benzyl-5'-ethyl-2'-hydroxy-2H-tetrazole-5-carboxanilide, there was prepared 3'-acetyl-5'-ethyl-2'-hydroxytetrazole-5-carboxanilide, m.p. 239°–241° C. (with decomposition).

EXAMPLE 10

Compounds D, Y, Z, AA and BB

Anhydrous aluminium chloride (2.84 g) was added carefully to cooled, dry tetrahydrofuran (35 ml), and the resulting solution was treated with sodium azide (4.14 g) and 3-acetyl-5-ethyl-2-hydroxy-cyanoformanilide (1.6 g). The mixture was stirred and heated at reflux for 24 hours and was then poured into a mixture of ice (100 g) and concentrated hydrochloric acid (20 ml). The yellow solid which precipitated was filtered off and recrystallised from acetonitrile to give 3'-acetyl-5'-ethyl-2'-hydroxytetrazole-5-carboxanilide (0.55 g), m.p. 239°–248° C. (with decomposition).

By proceeding in a similar manner, but replacing the 3-acetyl-5-ethyl-2-hydroxy-cyanoformanilide, used as a starting material, by the appropriate quantities of 3-acetyl-2-hydroxy-5-propyl-cyanoformanilide;
3-acetyl-2-hydroxy-cyanoformanilide;
5-ethyl-2-hydroxy-3-propionyl-cyanoformanilide; and
2-hydroxy-5-methyl-3-propionyl-cyanoformanilide;

respectively, there were prepared:

3'-acetyl-2'-hydroxy-5'-propyltetrazole-5-carboxanilide, m.p. 179°–180° C. (with decomposition);
3'-acetyl-2'-hydroxytetrazole-5-carboxanilide, m.p. 239°–241° C. (with decomposition) (recrystallised from glacial acetic acid);
5'-ethyl-2'-hydroxy-3'-propionyltetrazole-5-carboxanilide, m.p. 225°–226° C. (with decomposition) (recrystallised from glacial acetic acid); and
2'-hydroxy-5'-methyl-3'-propionyltetrazole-5-carboxanilide, m.p. 230°–232° C. (with decomposition) (recrystallised from ethanol).

EXAMPLE 11

Compounds CC and T

Aluminium chloride (2.17 g) was added cautiously to dry tetrahydrofuran (30 ml) at 0° C. The resulting solution was treated with sodium azide (3.08 g), followed by 2-benzyloxy-5-bromo-3-methoxy-cyanoformanilide (1.9 g). The mixture was then stirred and heated at reflux for 24 hours. The mixture was then poured into a mixture of ice (50 g) and concentrated hydrochloric acid (10 ml) and stirring was resumed for a further period of one hour. The resulting oily solid was extracted with ethyl acetate. The ethyl acetate was removed in vacuo and the residue was digested in aqueous ammonia solution (2 N). The resulting hot solution was treated with charcoal, filtered, and acidified by treatment with concentrated hydrochloric acid to give a buff solid which was filtered off and recrystallised from water, to give 5'-bromo-2'-hydroxy-3'-methoxytetrazole-5-carboxanilide (0.9 g), m.p. 217°–219° C. (with decomposition).

By proceeding in a similar manner, but replacing the 2-benzyloxy-5-bromo-3-methoxy-cyanoformanilide, used as a starting material, by the appropriate quantity of 2-benzyloxy-3-methoxy-5-methyl-cyanoformanilide, there was prepared 2'-hydroxy-3'-methoxy-5'-methyltetrazole-5-carboxanilide, m.p. 220°–222° C. (with decomposition).

EXAMPLE 12

Compound DD, EE, FF and GG

A stirred mixture of anhydrous sodium carbonate (0.6 g), hydroxylamine hydrochloride (1.1 g), water (1.0 ml) and N-methylpyrrolid-2-one (10.5 ml) was heated at 90° C. for 15 minutes. 3'-Acetyl-2'-hydroxy-5'-methyltetrazole-5-carboxanilide (1.0 g) was then added to the mixture, which was heated at 90°–95° C., with stirring, for 24 hours. The resulting solution was cooled and poured into aqueous hydrochloric acid (2 N; 50 ml). The precipitate was filtered off and recrystallised from a mixture of dimethylformamide and water to give 2'-hydroxy-3'-(1-hydroxyimino)ethyl-5'-methyltetrazole-5-carboxanilide (0.4 g), m.p. 245°–247° C. (with decomposition).

By proceeding in a similar manner, but replacing the hydroxylamine hydrochloride, used as a starting material, by the appropriate quantity of O-methylhydroxylamine hydrochloride, there was prepared 2'-hydroxy-3'-(1-methoxyimino)ethyl-5'-methyltetrazole-5-carboxanilide, m.p. 271°–273° C. (with decomposition).

By proceeding in a similar manner, but replacing the 3'-acetyl-2'-hydroxy-5'-methyltetrazole-5-carboxanilide used as a starting material by the appropriate quantity of 3'-acetyl-5'-ethyl-2'-hydroxytetrazole-5-carboxanilide there was prepared 5'-ethyl-2'-hydroxy-3'-(1-hydroxyimino)ethyltetrazole-5-carboxanilide, m.p. 232°–233° C. (with decomposition).

By again proceeding in a similar manner, but replacing the 3'-acetyl-2'-hydroxy-5'-methyltetrazole-5-carboxanilide and hydroxylamine hydrochloride used as starting materials by the appropriate quantities of 3'-acetyl-5'-ethyl-2'-hydroxytetrazole-5-carboxanilide and O-methylhydroxylamine hydrochloride, respectively, there was prepared 5'-ethyl-2'-hydroxy-3'-(1-methoxyimino)ethyltetrazole-5-carboxanilide, m.p. 257°–259° C. (with decomposition).

EXAMPLE 13

Compound D

A solution of dry dimethylformamide (1.5 ml) in dry acetonitrile (3.6 ml) at −20° C. was treated, dropwise with stirring, with a solution of oxalyl chloride (0.53 ml) in dry acetonitrile (0.6 ml). The resulting white suspension was stirred at −20° C. for 15 minutes and was then treated with the dipotassium salt of tetrazole-5-carboxylic acid (1.14 g), and the mixture was stirred at −20° C. for 20 minutes. The resulting mixture was treated with a solution of 3-amino-5-ethyl-2-hydroxyacetophenone (1.08 g) in dry pyridine (2 ml), and allowed to warm to room temperature and was stirred for 20 hours. The reaction mixture was then treated with a mixture of dichloromethane (30 ml) and aqueous sodium carbonate solution (2 N; 20 ml). The dichloromethane layer was separated and the aqueous layer was washed with a further quantity of dichloromethane (20 ml) and was acidified to pH 1 by treatment with concentrated hydrochloric acid. The resulting orange solids was filtered off, washed with water, and recrystallised from glacial acetic acid (20 ml) to give 3'-acetyl-5'-ethyl-2'-hydroxytetrazole-5-carboxanilide (0.55 g), m.p. 243°–245° C.

EXAMPLE 14

Compound D

A mixture of N,N-dimethyl(chloromethyleneimmonium) chloride (0.26 g), the dipotassium salt of tetrazole-5-carboxylic acid (0.38 g) and dry dimethylformamide (15 ml) was stirred at room temperature for 30 minutes. 3-Amino-5-ethyl-2-hydroxyacetophenone (0.36 g) was then added and the mixture was stirred at room temperature overnight. A mixture of dichloromethane (20 ml) and aqueous sodium carbonate solution (2 N; 20 ml) was added, the mixture was shaken thoroughly, and the aqueous layer was separated. The dichloromethane layer was again washed with aqueous sodium carbonate solution (2 N; 20 ml). The aqueous layers were combined and acidified to pH 1 by treatment with concentrated hydrochloric acid to give 3'-acetyl-5'-ethyl-2'-hydroxytetrazole-5-carboxanilide (0.12 g), m.p. 240°–242° C.

EXAMPLE 15

Compounds B and D

A solution of 3'-acetyl-1-benzyl-2'-hydroxy-5'-methyl-1H-tetrazole-5-carboxanilide (5.0 g) in glacial acetic acid was hydrogenated at 4.1 kg/cm² and 28° C., using a 5% w/w palladium on charcoal catalyst. The reaction was carefully monitored, and when the theoretical quantity of hydrogen had been used (after 9.5 hours) the catalyst was filtered off and extracted with acetic acid in a Soxhlet apparatus. The acetic acid solutions were then combined and evaporated, and the resulting residue was recrystallised from a mixture of dimethylformamide and water to give 3'-acetyl-2'-hydroxy-5'-methyltetrazole-5-carboxanilide (2.2 g), m.p. 257° C. (with decomposition).

By proceeding in a similar manner, but replacing the 3'-acetyl-1-benzyl-2'-hydroxy-5'-methyl-1H-tetrazole-5-carboxanilide used as starting material by the appropriate quantity of 3'-acetyl-5'-ethyl-1-benzyl-2'-hydroxy-1H-tetrazole-5-carboxanilide, there was prepared 3'-acetyl-5'-ethyl-2'-hydroxytetrazole-5-carboxanilide, m.p. 241°–243° C. (with decomposition).

REFERENCE EXAMPLE 1

A solution of 2-hydroxy-5-methyl-3-nitroacetophenone [4.0 g; Joshi et al., J. Amer. Chem. Soc., (1954), 76, 4993] in ethanol (150 ml) was hydrogenated at 25° C. and 3.5 kg/cm² for 44 minutes using a catalyst of platinum on charcoal. The solution was filtered and the filtrate was evaporated at 30° C. under diminished pressure to give a dark red oil, which set to a semi-solid on standing overnight. This material was purified by chromatography on a column of silica gel using diethyl ether as eluant. The fastest running band (yellow) was collected to give 3-amino-2-hydroxy-5-methylacetophenone (2.3 g), m.p. 56°–58° C., in the form of a bright yellow solid.

REFERENCE EXAMPLE 2

A solution of 2-hydroxy-3-nitroacetophenone [4.0 g; prepared by the method of Allen et al., J. Chem. Soc., (1949), 821] in ethanol (150 ml) was hydrogenated at 25° C. and 50 p.s.i. for 2.5 hours, using a catalyst of platinum on charcoal. The mixture was filtered and the filtrate was evaporated in vacuo to give a black solid, which was purified by chromatography on a column of silica gel, using diethyl ether as eluant. The fastest moving band (yellow) was collected to give 3-amino-2-hydroxyacetophenone (3.0 g), in the form of a bright yellow solid, m.p. 95°–97° C.

REFERENCE EXAMPLE 3

A stirred mixture of potassium 1-benzyl-1H-tetrazole-5-carboxylate (3.6 g; prepared as described in the specification of Belgian Pat. No. 845612), dry pyridine (0.75 ml) and dry toluene (65 ml) was cooled to 5° C. and treated with oxalyl chloride (12.5 ml). Stirring was maintained and the temperature was allowed to rise to 15° C. during a period of 2 hours. The mixture was filtered and the residue was washed with dry toluene. Evaporation of the combined toluene filtrate and washings, under diminished pressure, gave crude 1-benzyl-1H-tetrazole-5-carbonyl chloride in the form of an oil, which was used without further purification.

A solution of this acid chloride in dry methylene chloride (65 ml) was added to a stirred mixture of 2-benzyloxyaniline [3.0 g; prepared as described by Barber et al., J. Chem. Soc., (1961), 2828], pyridine (1.36 g) and dry methylene chloride (65 ml) at 0° C. The mixture was stirred at 10° C. for 2 hours and then was allowed to stand at room temperature overnight. The mixture was washed twice with water and the methylene chloride solution was then dried over magnesium sulphate and evaporated under diminished pressure. The resulting solid was recrystallised from ethanol to give 1-benzyl-2'-benzyloxy-1H-tetrazole-5-carboxanilide (3.1 g), m.p. 140°–142° C.

REFERENCE EXAMPLE 4

A solution of crude 1-benzyl-1H-tetrazole-5-carbonyl chloride (prepared from 0.73 g of potassium 1-benzyl-1H-tetrazole-5-carboxylate in the manner hereinbefore described in Reference Example 3) in dry methylene chloride (14 ml) was added to a stirred mixture of 3-amino-2-hydroxy-5-methylacetophenone (0.5 g) and pyridine (0.27 g) in dry methylene chloride (12 ml) at between 5° and 10° C. Stirring was maintained for 2 hours, allowing the temperature to rise to room temperature, and then the mixture was left to stand overnight. A further portion of methylene chloride (20 ml) was then added and the mixture was washed with water. The organic phase was dried over magnesium sulphate, and evaporated in vacuo to give a solid, which was recrystallised from ethanol, to give 3'-acetyl-1-benzyl-2'-hydroxy-5'-methyl-1H-tetrazole-5-carboxanilide (1.0 g), m.p. 183°–184° C.

REFERENCE EXAMPLE 5

A solution of crude 1-benzyl-1H-tetrazole-5-carbonyl chloride (prepared from 2.4 g of potassium 1-benzyl-1H-tetrazole-5-carboxylate in the manner hereinbefore described in Reference Example 3) in dry methylene chloride (50 ml) was added to a stirred solution of 3-amino-2-hydroxyacetophenone (1.5 g) and pyridine (0.9 g) in dry methylene chloride (40 ml) at 10° C. After standing at room temperature overnight, the solution was evaporated in vacuo and the resulting solid residue was recrystallised from a large volume of ethanol to give 3'-acetyl-1-benzyl-2'-hydroxy-1H-tetrazole-5-carboxanilide (1.5 g), in the form of pale yellow needles, m.p. 155°–157° C.

REFERENCE EXAMPLE 6

Potassium 1-(4-methoxybenzyl)-1H-tetrazole-5-carboxylate (10.0 g) and pyridine (1.8 ml) were stirred together in dry toluene (140 ml) at 10° C. Oxalyl chloride (30.7 ml) was added, and the mixture was stirred at 15° C. for 1 hour. The mixture was filtered and the residual solid was washed with dry toluene (100 ml). The filtrate and washings were combined and evaporated in vacuo to give crude 1-(4-methoxybenzyl)-1H-tetrazole-5-carbonyl chloride, which was used immediately in the next stage.

Similar material was obtained by proceeding in a similar manner but replacing the oxalyl chloride, used as a reagent, by the appropriate quantity of thionyl chloride.

A solution of the crude, fresh, 1-(4-methoxybenzyl)-1H-tetrazole-5-carbonyl chloride in dichloromethane (20 ml) was added dropwise to a solution of 3-amino-5-ethyl-2-hydroxyacetophenone (6.5 g) and pyridine (2.8 ml) in dry dichloromethane (140 ml) at 10° C., and the mixture was then allowed to warm up to 25° C. during a period of 2 hours. The reaction mixture was washed with water (2×150 ml) and with saturated aqueous sodium chloride solution (100 ml) and it was then dried over anhydrous sodium sulphate. Removal of the solvent in vacuo gave a solid, which was recrystallised from acetonitrile to give 3'-acetyl-5'-ethyl-2'-hydroxy-1-(4-methoxybenzyl)-1H-tetrazole-5-carboxanilide (10.1 g), m.p. 143°–145° C.

By proceeding in a similar manner, but replacing the 3-amino-5-ethyl-2-hydroxyacetophenone, used as a starting material, by the appropriate quantities of 3-amino-2-hydroxy-5-methylacetophenone;
3-amino-2-hydroxy-5-nitroacetophenone;
5-acetylamino-3-amino-2-hydroxyacetophenone;
3-amino-2-hydroxy-5-methylisobutyrophenone;
3-amino-5-cyano-2-hydroxyacetophenone;
3-amino-2-hydroxy-5-methylphenyl cyclopropyl ketone;
3-amino-2-hydroxy-5-methyl(trifluoroacetophenone);
3-amino-5-fluoro-2-hydroxyacetophenone;
3-amino-5-bromo-2-hydroxyacetophenone;
3-amino-2-hydroxy-5-methoxyacetophenone;
3-amino-5-cyano-2-hydroxypropiophenone;
6-amino-4-methyl-2-phenylacetylphenol; and
3-amino-2-hydroxy-5-(methylsulphonyl)acetophenone; respectively, there were prepared:

3'-acetyl-2'-hydroxy-1-(4-methoxybenzyl)-5'-methyl-1H-tetrazole-5-carboxanilide, m.p. 182°–185° C. (recrystallised from ethanol);

3'-acetyl-2'-hydroxy-1-(4-methoxybenzyl)-5'-nitro-1H-tetrazole-5-carboxanilide, m.p. 221°–223° C.;

3'-acetyl-5'-acetylamino-2'-hydroxy-1-(4-methoxybenzyl)-1H-tetrazole-5-carboxanilide, m.p. 170° C.;

2'-hydroxy-3'-isobutyryl-1-(4-methoxybenzyl)-5'-methyl-1H-tetrazole-5-carboxanilide, m.p. 144°–145° C. (recrystallised from a mixture of chloroform and ethanol);

3'-acetyl-5'-cyano-2'-hydroxy-1-(4-methoxybenzyl)-1H-tetrazole-5-carboxanilide, m.p. 228°–231° C.;

3'-cyclopropylcarbonyl-2'-hydroxy-1-(4-methoxybenzyl)-5'-methyl-1H-tetrazole-5-carboxanilide, m.p. 180°–182° C. (recrystallised from benzene);

2'-hydroxy-1-(4-methoxybenzyl)-5'-methyl-3'-trifluoroacetyl-1H-tetrazole-5-carboxanilide, m.p. 130°–131° C. [recrystallised from petroleum ether (b.p. 100°–120° C.)];

3'-acetyl-5'-fluoro-2'-hydroxy-1-(4-methoxybenzyl)-1H-tetrazole-5-carboxanilide, m.p. 180°–182° C.;

3'-acetyl-5'-bromo-2'-hydroxy-1-(4-methoxybenzyl)-1H-tetrazole-5-carboxanilide, m.p. 202°–204° C.;

3'-acetyl-2'-hydroxy-5'-methoxy-1-(4-methoxybenzyl)-1H-tetrazole-5-carboxanilide, m.p. 158°–161° C. (recrystallised from a mixture of acetonitrile and diethyl ether);

5'-cyano-2'-hydroxy-1-(4-methoxybenzyl)-3'-propionyl-1H-tetrazole-5-carboxanilide, m.p. 214°–216° C.;

2'-hydroxy-1-(4-methoxybenzyl)-5'-methyl-3'-phenylacetyl-1H-tetrazole-5-carboxanilide, m.p. 201°–204° C. (recrystallised from ethyl cellosolve); and 3'-acetyl-2'-hydroxy-1-(4-methoxybenzyl)-5'-methylsulphonyl-1H-tetrazole-5-carboxanilide, m.p. 234°–237° C.

By proceeding in a similar manner, but replacing the potassium 1-(4-methoxybenzyl)-1H-tetrazole-5-carboxylate by the appropriate quantity of potassium 2-(4-methoxybenzyl)-2H-tetrazole-5-carboxylate, there was prepared 3'-acetyl-5'-ethyl-2'-hydroxy-2-(4-methoxybenzyl)-2H-tetrazole-5-carboxanilide, m.p. 158°–161° C.

REFERENCE EXAMPLE 7

By proceeding in a manner similar to that described hereinbefore in Reference Example 3, but replacing the 2-benzyloxyaniline used as a starting material by the appropriate quantities of 2-benzyloxy-3-methoxyaniline and 2-benzyloxy-3-methoxy-5-ethylaniline, respectively, there were prepared:

1-benzyl-2'-benzyloxy-3'-methoxy-1H-tetrazole-5-carboxanilide, m.p. 145°–147° C. (recrystallised from ethanol); and 1-benzyl-2'-benzyloxy-5'-ethyl-3'-methoxy-1H-tetrazole-5-carboxanilide, m.p. 150°–151° C. (recrystallised from ethyl acetate).

REFERENCE EXAMPLE 8

By proceeding in a manner similar to that described hereinbefore in Reference Example 4, but replacing the 3-amino-2-hydroxy-5-methylacetophenone, used as a starting material, by the appropriate quantities of methyl 3-amino-2-hydroxy-5-methylbenzoate;
ethyl 3-amino-2-hydroxy-5-methylbenzoate;
3-amino-2-hydroxy-5-methyl-N,N-dimethylbenzamide;
3-amino-2-hydroxy-5-methyl-butyrophenone; and
3-amino-5-ethyl-2-hydroxy-butyrophenone; respectively, there were prepared:

1-benzyl-2'-hydroxy-3'-methoxycarbonyl-5'-methyl-1H-tetrazole-5-carboxanilide, m.p. 168°–170° C. (recrystallised from a mixture of chloroform and methanol);

1-benzyl-3'-ethoxycarbonyl-2'-hydroxy-5'-methyl-1H-tetrazole-5-carboxanilide, m.p. 189°–191° C. (recrystallised from a mixture of chloroform and ethanol;

1-benzyl-3'-(N,N-dimethylcarbamoyl)-2'-hydroxy-5'-methyl-1H-tetrazole-5-carboxanilide, m.p. 224°–225° C. (recrystallised from a mixture of chloroform and methanol);

1-benzyl-3'-butyryl-2'-hydroxy-5'-methyl-1H-tetrazole-5-carboxanilide, m.p. 166°–168.5° C. (recrystallised from a mixture of chloroform and ethanol); and 3'-acetyl-1-benzyl-5'-ethyl-2'-hydroxy-1H-tetrazole-5-carboxanilide, m.p. 175°–176° C. (recrystallised from acetonitrile).

By again proceeding in a similar manner, but replacing the 1-benzyl-1H-tetrazole-5-carbonyl chloride and 3-amino-2-hydroxy-5-methylacetophenone, used as starting materials, by the appropriate quantities of 2-benzyl-2H-tetrazole-5-carbonyl chloride and 3-amino-5-ethyl-2-hydroxyacetophenone, respectively, there was prepared 3'-acetyl-2-benzyl-5'-ethyl-2'-hydroxy-2H-tetrazole-5-carboxanilide, m.p. 160°–162° C. (recrystallised from ethanol).

REFERENCE EXAMPLE 9

A solution of 3'-acetyl-2'-hydroxy-1-(4-methoxybenzyl)-5'-nitro-1H-tetrazole-5-carboxanilide (2.06 g) in a solution of hydrogen chloride in ethanol (0.36 N; 60 ml) was hydrogenated at atmospheric pressure and at 25° C., using a 5% w/w palladium on charcoal catalyst (0.5 g), during a period of 150 minutes. The catalyst was then filtered off and the filtrate was evaporated in vacuo. The resulting residue was recrystallised from ethanol to give 3'-acetyl-5'-amino-2'-hydroxy-1-(4-methoxybenzyl)-1H-tetrazole-5-carboxanilide hydrochloride (1.2 g), in the form of colourless crystals, m.p. 225° C. (with decomposition).

REFERENCE EXAMPLE 10

A cooled mixture of dry pyridine (20 ml) and trifluoroacetic acid (0.3 ml) was treated with 3-amino-5-ethyl-2-hydroxyacetophenone (0.36 g), potassium 1-(4-methoxybenzyl)-1H-tetrazole-5-carboxylate (0.54 g) and dicyclohexylcarbodiimide (0.41 g), and the mixture was stirred at room temperature overnight. The mixture was then poured into a mixture of ice (10 g) and concentrated hydrochloric acid (20 ml), stirred for 1 hour and the resulting solid was filtered off and washed with water to give 3'-acetyl-5'-ethyl-2'-hydroxy-1-(4-methoxybenzyl)-1H-tetrazole-5-carboxanilide (0.82 g).

REFERENCE EXAMPLE 11

A stirred mixture of dry dimethylformamide (1.5 ml) and dry acetonitrile (3.45 ml) at −20° C. was treated with a solution of oxalyl chloride (0.53 g) in dry acetonitrile (0.58 ml). The resulting white suspension was diluted with a further quantity of acetonitrile (5 ml) and stirred at −20° C. for 15 minutes. Potassium 1-(4-methoxybenzyl)-1H-tetrazole-5-carboxylate (1.63 g) was then added and the mixture was stirred for a further 15 minutes at −20° C. A solution of 3-amino-5-ethyl-2-hydroxyacetophenone (1.08 g) in dry pyridine (2 ml) was added and the mixture was allowed to warm and was stirred at room temperature overnight. The mixture was then treated with aqueous sodium carbonate solution (2 N; 20 ml) and dichloromethane (30 ml), and the aqueous layer was removed and extracted with a further quantity of dichloromethane (15 ml). The combined organic layers were washed with water (2×25 ml), dried over magnesium sulphate and evaporated to give a yellow solid, which was recrystallised from ethanol, to give 3'-acetyl-5'-ethyl-2'-hydroxy-1-(4-methoxybenzyl)-1H-tetrazole-5-carboxanilide (0.83 g), m.p. 140°–142° C.

REFERENCE EXAMPLE 12

A mixture of 2-benzyloxy-3-methoxy-5-methylaniline (2.6 g), potassium 1-benzyl-1H-tetrazole-5-carboxylate (2.5 g) and dicyclohexylcarbodiimide (2.1 g) in dry pyridine (100 ml) was stirred at room temperature overnight. The mixture was then poured into a mixture of ice (250 g) and concentrated hydrochloric acid (100 ml), and the mixture was allowed to stand for 1 hour. The precipitate was filtered off and recrystallised from ethanol to give 1-benzyl-2'-benzyloxy-3'-methoxy-5'-methyl-1H-tetrazole-5-carboxanilide (0.16 g), m.p. 181°–183° C.

REFERENCE EXAMPLE 13

A mixture of 3-amino-5-ethyl-2-hydroxyacetophenone (0.45 g), 2-(4-methoxybenzyl)-2H-tetrazole-5-carboxylic acid (0.58 g) and dicyclohexylcarbodiimide (0.52 g) in dry pyridine (15 ml) was stirred at room temperature overnight, and was then poured into a mixture of ice (75 g) and concentrated hydrochloric acid (25 ml). After stirring for 30 minutes, the resulting yellow solid was filtered off, washed well with water and recrystallised from ethanol to give 3'-acetyl-5'-ethyl-2'-hydroxy-2-(4-methoxybenzyl)-2H-tetrazole-5-carboxanilide (0.5 g), m.p. 159°–160° C.

REFERENCE EXAMPLE 14

A mixture of 3-amino-5-ethyl-2-hydroxyacetophenone (0.9 g), 2-benzyl-2H-tetrazole-5-carboxylic acid (1.02 g), dicyclohexylcarbodiimide (1.03 g) and dry sulpholane (35 ml) was stirred at room temperature overnight. The resulting yellow solid was filtered off, washed with water, and recrystallised from ethanol to give 3'-acetyl-2-benzyl-5'-ethyl-2'-hydroxy-2H-tetrazole-5-carboxanilide (0.93 g), m.p. 159°–161° C.

REFERENCE EXAMPLE 15

A solution of carbonyl dicyanide in diethyl ether (30 ml; prepared in situ from tetracyanoethylene oxide by a method described in the specification of U.S. Pat. No.

3,115,517) at 0° C. was treated with a solution of 3-amino-2-hydroxyacetophenone (3.15 g) in anhydrous diethyl ether (20 ml) during a period of 20 minutes and the mixture was stirred for a further period of one hour. The solvents were removed in vacuo at 10° C. to give a brown oil, which was extracted with boiling toluene (250 ml) and the extract was treated with charcoal, concentrated to a small volume and cooled to give 3-acetyl-2-hydroxy-cyanoformanilide (2.0 g) in the form of pale yellow crystals, m.p. 139°–141° C.

By proceeding in a similar manner, but replacing the 3-amino-2-hydroxyacetophenone, used as a starting material, by the appropriate quantities of
3-amino-5-ethyl-2-hydroxyacetophenone;
3-amino-2-hydroxy-5-propylacetophenone;
3-amino-5-ethyl-2-hydroxypropiophenone; and
3-amino-2-hydroxy-5-methylpropiophenone, respectively, there were prepared:
3-acetyl-5-ethyl-2-hydroxy-cyanoformanilide, m.p. 130°–132° C.;
3-acetyl-2-hydroxy-5-propyl-cyanoformanilide, m.p. 124°–125° C.;
5-ethyl-2-hydroxy-3-propionyl-cyanoformanilide, m.p. 138.5°–140° C.; and
2-hydroxy-5-methyl-3-propionyl-cyanoformanilide, m.p. 144°–147° C.

By again proceeding in a similar manner, but replacing the toluene, used as a solvent, by petroleum ether (b.p. 60°–80° C.) and replacing the 3-amino-2-hydroxyacetophenone by the appropriate quantities of
2-benzyloxy-5-bromo-3-methoxyaniline; and
2-benzyloxy-3-methoxy-5-methylaniline; respectively, there were prepared:
2-benzyloxy-5-bromo-3-methoxy-cyanoformanilide, m.p. 85° C. (with decomposition); and
2-benzyloxy-3-methoxy-5-methyl-cyanoformanilide, m.p. 94°–95° C.

REFERENCE EXAMPLE 16

A mixture of ethyl 1-benzyl-2H-tetrazole-5-carboxylate and ethyl 2-benzyl-2H-tetrazole-5-carboxylate (7 g; prepared as described below and still containing a little sulpholane) was dissolved in hot ethanol (100 ml) and the hot solution was treated with a solution of potassium hydroxide (2.7 g) in water (8 ml). The white solid which separated was filtered off from the hot solution and washed with ethanol to give potassium 2-benzyl-2H-tetrazole-5-carboxylate (4.64 g), m.p. 264°–267° C. [The pure salt, obtained as a hemihydrate after recrystallisation from water, had a melting point of 272°–273° C.]

The hot filtrate was cooled and allowed to stand, to give potassium 1-benzyl-1H-tetrazole-5-carboxylate (2.5 g), m.p. 197°–199° C. (with decomposition).

A suspension of sodium hydride (0.13 g) in dry sulpholane (10 ml) was treated with ethyl tetrazole-5-carboxylate (0.71 g), and the mixture stirred for 20 minutes at room temperature. Benzyl chloride (0.7 g) was then added, and the mixture was stirred at 60°–65° C. overnight. The mixture was then poured onto ice (25 g) and the resulting oil was separated off and dissolved in diethyl ether (35 ml). The aqueous layer was extracted with a further quantity of diethyl ether (10 ml) and the combined ether extracts were dried over magnesium sulphate. Removal of the ether under reduced pressure gave a mixture (1.36 g) of ethyl 1-benzyl-1H-tetrazole-5-carboxylate and ethyl 2-benzyl-2H-tetrazole-5-carboxylate, containing a little sulpholane.

Ethyl tetrazole-5-carboxylate was prepared by the following methods:

(a) Ethyl cyanoformate (2.5 g) was dissolved in dry pyridine (10 ml) and the stirred solution was treated with a cooled mixture of trifluoroacetic acid (4.4 ml) and dry pyridine (15 ml). The stirred suspension was treated with sodium azide (1.8 g) and the resulting mixture was stirred at 60°–65° C. for 48 hours. The mixture was cooled to room temperature and poured onto a mixture of ice and concentrated hydrochloric acid (100 g), and extracted with diethyl ether (3×30 ml) and the combined ethereal extracts were dried over magnesium sulphate and evaporated to dryness to give an oil [which partially crystallised on trituration with petroleum ether (b.p. 40°–60° C.)] which was purified by chromatography on silica gel, eluting with a mixture (1:1 v/v) of petroleum ether (b.p. 40°–60° C.) and diethyl ether, to give ethyl tetrazole-5-carboxylate, (1.57 g), m.p. 88°–93° C.

(b) By proceeding in a similar manner, but replacing the pyridine by the appropriate quantity of 2,6-dimethylpyridine, there was obtained ethyl tetrazole-5-carboxylate, m.p. 80°–92° C., in a yield of 35%.

(c) A solution of trimethylsilylazide (0.58 g) and ethyl cyanoformate (0.5 g) in dry benzene (20 ml) was heated at reflux for 48 hours. The solution was allowed to stand at room temperature for 4 days, and the resulting white solid was filtered off to give ethyl tetrazole-5-carboxylate (0.3 g), m.p. 88°–93° C.

(d) By proceeding in a similar manner, but replacing the benzene by the appropriate quantity of ethyl acetate, there was obtained ethyl tetrazole-5-carboxylate (0.5 g), m.p. 86°–90° C.

(e) A solution of tributyltin azide (6.65 g) and ethyl cyanoformate (1.98 g) in dry benzene (25 ml) was heated at reflux for 48 hours. The benzene was removed under reduced pressure and the residue was dissolved in an excess quantity of a dry solution of hydrogen chloride in ethanol. The mixture was allowed to stand, and then the ethanol was removed in vacuo on the rotary evaporator to give a red oil. Chromatography of this oil on a column of silica gel, eluting with a mixture of methanol and chloroform (1:9 v/v), gave ethyl tetrazole-5-carboxylate, identical with samples prepared by the other methods as described above.

REFERENCE EXAMPLE 17

A mixture of ethyl 1-(4-methoxybenzyl)-1H-tetrazole-5-carboxylate and ethyl 2-(4-methoxybenzyl)-2H-tetrazole-5-carboxylate (11.7 g) (prepared as described below and still containing a little sulpholane) was dissolved in hot ethanol (165 ml) and the solution was treated with a solution of potassium hydroxide (4.5 g) in water (13.5 ml). The mixture was cooled and the white crystalline solid which separated was filtered off to give potassium 2-(4-methoxybenzyl)-2H-tetrazole-5-carboxylate (4.3 g), m.p. 271°–273° C. (with decomposition). [The pure salt, obtained as a hemihydrate after recrystallisation from water, had a melting point of 273°–274° C. (with decomposition)].

The filtrate was concentrated further and filtered to give potassium 1-(4-methoxybenzyl)-1H-tetrazole-5-carboxylate (3.14 g), m.p. 192°–194° C. (with decomposition).

A suspension of sodium hydride (1.3 g) in dry sulpholane (100 ml) was treated with ethyl tetrazole-5-carboxylate (7.1 g), and the mixture was stirred at room temperature for 30 minutes. 4-Methoxybenzyl chloride (9.0 g) was added, and the mixture was stirred at 60°–65° C. overnight. The mixture was then poured on to ice, and the yellow oil was separated from the aqueous layer and dissolved in diethyl ether (300 ml). The ethereal solution was dried over magnesium sulphate and evaporated to give a residue (11.7 g) of a mixture of ethyl 1-(4-methoxybenzyl)-1H-tetrazole-5-carboxylate and ethyl 2-(4-methoxybenzyl)-2H-tetrazole-5-carboxylate, containing a little sulpholane.

REFERENCE EXAMPLE 18

Ethyl tetrazole-5-carboxylate (0.36 g) was dissolved in hot ethanol (7.5 ml) and the solution was treated with a solution of potassium hydroxide (0.22 g) in water (0.7 ml). The resulting white solid was filtered off, and washed with ethanol to give the dipotassium salt of tetrazole-5-carboxylic acid (0.16 g), which did not melt below 330° C.

REFERENCE EXAMPLE 19

A mixture of freshly prepared benzyl azide (1.3 g) and ethyl cyanoformate (1.0 g) in xylene (10 ml) was heated at reflux for 48 hours. The mixture was evaporated under reduced pressure and below 40° C. to give a residue of ethyl 1-benzyl-1H-tetrazole-5-carboxylate (2.13 g).

By proceeding in a similar manner, but replacing the xylene by the appropriate quantity of butyl acetate, there was prepared ethyl 1-benzyl-1H-tetrazole-5-carboxylate in a yield of 55%.

By again proceeding in a similar manner but heating at between 95° and 100° C. for 8 days instead of at reflux for 48 hours, and replacing the xylene by the appropriate quantities of toluene and butyl acetate respectively, the yield of ethyl 1-benzyl-1H-tetrazole-5-carboxylate obtained was 70% when toluene was used and 81% when butyl acetate was used.

REFERENCE EXAMPLE 20

A mixture of crude 4-methoxybenzyl azide (45.3 g; prepared as described below) and ethyl cyanoformate (33 g) in xylene (300 ml) was heated at reflux for 48 hours. The mixture was evaporated at below 40° C. and under reduced pressure to leave a residue of ethyl 1-(4-methoxybenzyl)-1H-tetrazole-5-carboxylate (69.36 g), m.p. 52° C.

By proceeding in a similar manner, but replacing the xylene by the appropriate quantities of chlorobenzene, toluene and butyl acetate, there was prepared ethyl 1-(4-methoxybenzyl)-1H-tetrazole-5-carboxylate in yields of 62%, 55% and 44%, respectively.

By again proceeding in a similar manner, but using an excess (3-fold) of ethyl cyanoformate instead of the xylene, and heating at 110° C. for 36 hours instead of at reflux for 48 hours, there was obtained ethyl 1-(4-methoxybenzyl)-1H-tetrazole-5-carboxylate in a yield of 72%.

A solution of freshly prepared 4-methoxybenzyl chloride (45.85 g) in dry dimethylformamide (150 ml) was treated with sodium azide (19.35 g). The stirred mixture was heated at between 100° and 110° C. for 20 hours, and was then cooled and poured into water (1200 ml). The resulting oil was extracted with diethyl ether (2×500 ml) and the combined ethereal extracts were washed with water (2×250 ml), dried over magnesium sulphate, and evaporated to give crude 4-methoxybenzyl azide (45.3 g).

By proceeding in a similar manner, but replacing the dimethylformamide by the appropriate quantities of N-methylpyrrolid-2-one and sulpholane, there was obtained 4-methoxybenzyl azide in yields of 73% and 72%, respectively.

REFERENCE EXAMPLE 21

Potassium 2-(4-methoxybenzyl)-2H-tetrazole-5-carboxylate (2.45 g) was dissolved in a minimum quantity of water and acidified to pH 1 by treatment with concentrated hydrochloric acid. The mixture was stirred for 3 hours, and then the solid was filtered off and washed with water to give 2-(4-methoxybenzyl)-2H-tetrazole-5-carboxylic acid (1.20 g), m.p. 146°–147° C. (with decomposition).

REFERENCE EXAMPLE 22

Potassium 2-benzyl-2H-tetrazole-5-carboxylate (2.42 g) was suspended in water (10 ml) and the mixture was warmed until it dissolved. The solution was cooled in ice and strongly acidified by treatment with concentrated hydrochloric acid to give 2-benzyl-2H-tetrazole-5-carboxylic acid (1.46 g), m.p. 127°–130° C.

REFERENCE EXAMPLE 23

A solution of 2-hydroxy-3,5-dinitroacetophenone (4.0 g) and ammonium chloride (11.4 g) in methanol (100 ml) was heated at reflux and treated with sodium sulphide (12.8 g). The mixture was heated and stirred for a further period of 10 minutes, during which further quantities of ammonium chloride (11.4 g) and sodium sulphide (12.8 g) were added. After a further period of 30 minutes at reflux, further quantities of ammonium chloride (11.4 g) and sodium sulphide (12.8 g) were added, and heating was continued for 2 hours. The mixture was then poured into water (200 ml) and the resulting precipitate was filtered off. This solid was heated at reflux with ethanol (18 ml) and concentrated hydrochloric acid (12 ml) for 30 minutes and then poured into water (50 ml). The solution was filtered and the aqueous filtrate was adjusted to pH 5 by treatment with concentrated aqueous sodium hydroxide solution. The crystalline mass formed was filtered off and recrystallised from ethanol to give 3-amino-2-hydroxy-5-nitroacetophenone (1.9 g), m.p. 172°–175° C.

REFERENCE EXAMPLE 24

A suspension of 5-ethyl-2-hydroxy-3-nitroacetophenone (14.7 g) in ethanol (250 ml) was hydrogenated at 25° C. and at atmospheric pressure, using a 5% (w/w) palladium on charcoal catalyst (1.5 g). The catalyst was filtered off and the filtrate was evaporated in vacuo, giving a dark residue, which was extracted with boiling petroleum ether (b.p. 60°–80° C.; 150 ml). The extract was cooled and filtered to give 3-amino-5-ethyl-2-hydroxyacetophenone (8.8 g) in the form of yellow crystals, m.p. 50°–51° C.

By proceeding in a similar manner, but replacing the 5-ethyl-2-hydroxy-3-nitroacetophenone used as starting material by the appropriate quantities of
2-hydroxy-3-nitro-5-propylacetophenone;
2-hydroxy-5-methyl-3-nitropropiophenone;
5-fluoro-2-hydroxy-3-nitroacetophenone;
5-acetylamino-2-hydroxy-3-nitroacetophenone;
2-hydroxy-5-methyl-3-nitro-isobutyrophenone;
methyl 2-hydroxy-5-methyl-3-nitrobenzoate;
ethyl 2-hydroxy-5-methyl-3-nitrobenzoate;
N,N-dimethyl-2-hydroxy-5-methyl-3-nitrobenzamide;

2-hydroxy-5-methyl-3-nitrobutyrophenone;
2-hydroxy-5-methylsulphonyl-3-nitroacetophenone; and
5-ethyl-2-hydroxy-3-nitropropiophenone; respectively, there were prepared:

3-amino-2-hydroxy-5-propylacetophenone, m.p. 43°–45° C.;
3-amino-2-hydroxy-5-methylpropiophenone, m.p. (of crude material) about 40° C.;
3-amino-5-fluoro-2-hydroxyacetophenone;
5-acetylamino-3-amino-2-hydroxyacetophenone;
3-amino-2-hydroxy-5-methyl-isobutyrophenone, m.p. 41°–42° C.;
methyl 3-amino-2-hydroxy-5-methylbenzoate, m.p. 65°–68° C. [recrystallised from petroleum ether (b.p. 80°–100° C.)];
ethyl 3-amino-2-hydroxy-5-methylbenzoate; m.p. 92°–93° C. (recrystallised from a mixture of ethanol and water);
3-amino-2-hydroxy-5-methyl-N,N-dimethylbenzamide, m.p. 108° C. [recrystallised from petroleum ether (b.p. 100°–120° C.)];
3-amino-2-hydroxy-5-methylbutyrophenone, m.p. 79°–81° C. (recrystallised from methanol);
3-amino-2-hydroxy-5-methylsulphonyl-acetophenone; and
3-amino-5-ethyl-2-hydroxypropiophenone, m.p. 30° C. [recrystallised from petroleum ether (b.p. 40°–60° C.)].

By proceeding in a similar manner, but using a 5% (w/w) platinum on charcoal catalyst and replacing the 5-ethyl-2-hydroxy-3-nitroacetophenone, used as a starting material, by cyclopropyl 2-hydroxy-5-methyl-3-nitrophenyl ketone;
2-hydroxy-5-methyl-3-nitro-trifluoroacetophenone;
4-methyl-6-nitro-2-phenylacetylphenol;
2-benzyloxy-3-methoxy-5-methylnitrobenzene;
2-benzyloxy-5-ethyl-3-methoxynitrobenzene, and
2-benzyloxy-5-bromo-3-methoxynitrobenzene; respectively,
there were prepared:
cyclopropyl 3-amino-2-hydroxy-5-methylphenyl ketone, m.p. 79.5°–80° C.;
3-amino-2-hydroxy-5-methyltrifluoroacetophenone, m.p. 87°–88° C. [recrystallised from petroleum ether (b.p. 40°–60° C.)];
6-amino-4-methyl-2-phenylacetylphenol, m.p. 74°–76° C. [recrystallised from petroleum ether (b.p. 40°–60° C.)];
2-benzyloxy-3-methoxy-5-methylaniline;
2-benzyloxy-5-ethyl-3-methoxyaniline; and
2-benzyloxy-5-bromo-3-methoxyaniline.

REFERENCE EXAMPLE 25

A mixture of 5-bromo-2-hydroxy-3-nitroacetophenone (6.25 g), toluene (20 ml) and aqueous titanium trichloride solution (20% w/v; 115 ml) was shaken for 20 hours in a sealed flask at an internal pressure of 6 cm Hg. The mixture was then basified by treatment with aqueous ammonia solution (s.g. 0.880) and then was extracted with chloroform (3×50 ml). The combined organic layers were washed with water (3×15 ml), dried over anhydrous sodium sulphate and evaporated to give an orange solid which was purified by column chromatography on silica gel, using diethyl ether as eluant, the fastest moving band being collected to give 3-amino-5-bromo-2-hydroxyacetophenone, m.p. 99°–102° C.

REFERENCE EXAMPLE 26

A solution of 5-cyano-2-hydroxy-3-nitropropiophenone (3.0 g) in ethanol (75 ml) was hydrogenated at atmospheric pressure and at 25° C., using 5% palladium on charcoal as catalyst (0.3 g). The mixture was filtered and the filtrate was evaporated in vacuo. The residue was subjected to chromatography on a silica gel column (150 g), using diethyl ether as eluant, the fastest moving band being collected, to give 3-amino-5-cyano-2-hydroxypropiophenone (1.8 g), m.p. 144°–146° C.

By proceeding in a similar manner, but replacing the 5-cyano-2-hydroxy-3-nitropropiophenone used as starting material by the appropriate quantity of 5-cyano-2-hydroxy-3-nitroacetophenone, there was prepared 3-amino-5-cyano-2-hydroxyacetophenone, m.p. 146°–148° C.

REFERENCE EXAMPLE 27

A solution of 2-hydroxy-5-methyl-isobutyrophenone (7.12 g) in dry dichloromethane (140 ml) was treated with a solution of fuming nitric acid (1.8 ml; s.g. 1.5) in glacial acetic acid (18 ml). The mixture was left to stand for 6 hours at room temperature, and then was washed 3 times with water (100 ml, 50 ml, 50 ml). The organic phase was dried over anhydrous sodium sulphate and evaporated in vacuo to give a yellow solid, which was recrystallised from methanol at −70° C. to give 2-hydroxy-5-methyl-3-nitro-isobutyrophenone (6.75 g), m.p. 75°–77° C.

By proceeding in a similar manner, but replacing the 2-hydroxy-5-methyl-isobutyrophenone used as starting material by the appropriate quantities of 2-hydroxy-5-methylbutyrophenone;
cyclopropyl 2-hydroxy-5-methylphenyl ketone;
4-methyl-2-phenylacetylphenol; and
2-hydroxy-5-methyltrifluoroacetophenone, respectively,
there were prepared:
2-hydroxy-5-methyl-3-nitrobutyrophenone, m.p. 72°–74° C. (recrystallised from ethanol);
cyclopropyl 2-hydroxy-5-methyl-3-nitrophenyl ketone, m.p. 122°–125° C. (recrystallised from ethanol);
4-methyl-6-nitro-2-phenylacetylphenol, m.p. 80°–82° C. (recrystallised from ethanol); and
2-hydroxy-5-methyl-3-nitrotrifluoroacetophenone, m.p. 49°–50° C. [heated at 110°–120° C./15 mm Hg for 2 hours and then recrystallised from petroleum ether (b.p. 40°–60° C.)].

REFERENCE EXAMPLE 28

5-Fluoro-2-hydroxyacetophenone (20.0 g) was dissolved in concentrated sulphuric acid (150 ml), and the mixture was cooled to −20° C. A mixture of concentrated nitric acid (17.0 ml; s.g. 1.42) in concentrated sulphuric acid (18.0 ml) was then added to it, dropwise with stirring, keeping the temperature of the reaction mixture between −15° and −5° C. The reaction mixture was then allowed to warm up to −5° C. and was poured into iced water (2 liters). The yellow precipitated product was filtered off and recrystallised from ethanol to give 5-fluoro-2-hydroxy-3-nitroacetophenone (11.9 g), m.p. 87°–90° C.

By proceeding in a similar manner, but replacing the 5-fluoro-2-hydroxyacetophenone used as starting material by the appropriate quantities of 5-ethyl-2-hydroxyacetophenone;
2-hydroxy-5-propylacetophenone;
5-cyano-2-hydroxyacetophenone;
5-ethyl-2-hydroxypropiophenone;
5-cyano-2-hydroxypropiophenone; and
2-hydroxy-5-methylsulphonylacetophenone; respectively,
there were prepared:
5-ethyl-2-hydroxy-3-nitroacetophenone, m.p. 120°–122° C.;
2-hydroxy-3-nitro-5-propylacetophenone, m.p. 67°–69° C.;
5-cyano-2-hydroxy-3-nitroacetophenone, m.p. 137°–140° C.;
5-ethyl-2-hydroxy-3-nitropropiophenone, m.p. 86.5°–87.5° C.;
5-cyano-2-hydroxy-3-nitropropiophenone, m.p. 90° C.; and
2-hydroxy-5-methylsulphonyl-3-nitroacetophenone, m.p. 189°–191° C.

REFERENCE EXAMPLE 29

A solution of fuming nitric acid (12.1 ml; s.g. 1.5) in glacial acetic acid (120 ml) was added in one portion to a stirred solution of 4-ethyl-2-methoxyphenol (41.7 g) in dry dichloromethane (800 ml). After 1 minute the solution was washed with water (3×300 ml), and the organic layer was dried over anhydrous sodium sulphate and evaporated in vacuo to give an orange crystalline residue. This was recrystallised from a mixture of methanol and water to give 4-ethyl-2-methoxy-6-nitrophenol (31.3 g), m.p. 59°–61° C.

By proceeding in a similar manner but replacing the 4-ethyl-2-methoxyphenol used as starting material by the appropriate quantity of 4-bromo-2-methoxyphenol, there was prepared 4-bromo-2-methoxy-6-nitrophenol, m.p. 108°–110° C. (recrystallised from ethanol).

REFERENCE EXAMPLE 30

A solution of 4-methylphenyl 4-chlorobutyrate (26.8 g) in redistilled nitrobenzene (120 ml) was treated with anhydrous aluminium chloride (25.2 g), in portions with stirring. The mixture was heated at 60°–70° C. for 8 hours and was then cooled and poured into a mixture of ice (300 g) and concentrated hydrochloric acid (30 ml) and extracted twice with diethyl ether. The combined ethereal extracts were then washed with water (3×20 ml) and dried over anhydrous sodium sulphate and evaporated in vacuo to give a brown oil, which was distilled to give 2-hydroxy-5-methyl-(4-chlorobutyrophenone) (17.9 g), b.p. 135°–136° C./0.3 mm Hg, m.p. 36°–38° C.

REFERENCE EXAMPLE 31

4-Methylphenyl trifluoroacetate (36 g) was added dropwise to a stirred suspension of aluminium chloride (27 g) in carbon disulphide (35 ml) at 25° C., over a period of 1 hour. The mixture was then heated under reflux for 1 hour. The solvent was then distilled off, an operation which lasted 90 minutes, the temperature of the reaction was gradually raised to 115° C. during 15 minutes, and then the mixture was cooled to 90° C. and kept at 90° C. for 90 minutes. The resulting mixture was cooled to room temperature, treated with ice cold aqueous hydrochloric acid (2 N; 300 ml), and steam distilled. The distillate was extracted with diethyl ether (3×150 ml) and then the extract was evaporated to give a yellow oil (30.8 g). A solution of this oil in ethanol (470 ml) was added to a solution of cupric acetate (26 g) in water (780 ml) and then the mixture was treated with aqueous ammonia solution (s.g. 0.880; 52 ml). The mixture was left to stand for 24 hours. The resulting green solid was filtered off, mixed with hydrochloric acid (2 N; 300 ml) and heated at 50° C. The suspension was then cooled, and extracted with diethyl ether (3×50 ml), and after evaporation of the solvent there was obtained a dark oil. Distillation and collection of the b.p. 90°–120° C./30 mm Hg fraction gave a yellow oil, which solidified on scratching. This material was recrystallised from petroleum ether (b.p. 60°–80° C.) at −70° C. to give 2-hydroxy-5-methyltrifluoroacetophenone (9.0 g), m.p. 40.5°–42° C.

4-Methylphenol (54 g) was treated with trifluoroacetic anhydride (110 g). The mixture was heated to 40° C., whereupon a vigorous reaction occurred. After the reaction had subsided, the mixture was heated at 90°–95° C. for 30 minutes and distilled to give 4-methylphenyl trifluoroacetate (92 g), b.p. 169°–170° C.

REFERENCE EXAMPLE 32

An intimate mixture of 4-cyanophenyl propionate (90.0 g) and aluminium chloride (245 g) was heated at 180° C. for 3 hours. After cooling, the resulting solid was ground to a powder and added cautiously to a stirred solution of concentrated hydrochloric acid (225 ml) in water (1500 ml). The mixture was stirred for 1 hour and then the resulting solid was filtered off and recrystallised from a mixture of ethanol and water to give 5-cyano-2-hydroxypropiophenone (65.0 g), m.p. 130°–132° C.

4-Cyanophenol (119 g) and propionic anhydride (140 g) were heated together at 170° C. for 90 minutes with occasional mild agitation of the reaction vessel. The mixture was then cooled and poured into iced water (1000 ml), whereupon an oil was obtained. This oil was separated and it then solidified. It was recrystallised from a mixture of ethanol and water to give 4-cyanophenyl propionate (95 g), m.p. 44°–46° C.

REFERENCE EXAMPLE 33

A stirred suspension of aluminium chloride (88.9 g) in dichloromethane (500 ml) was treated with 4-ethylphenol (40.7 g), portionwise. Redistilled propionyl chloride (28.95 ml) was then added cautiously, during 15 minutes. The mixture was stirred and heated at reflux for 24 hours and was then poured cautiously into a mixture of ice (1000 g) and concentrated hydrochloric acid (200 ml) and the mixture was stirred for 30 minutes. The organic layer was separated, washed with water (3×100 ml), dried over anhydrous sodium sulphate, and evaporated to give a brown oil. Distillation of this oil gave 5-ethyl-2-hydroxypropiophenone (35.2 g), b.p. 80°–82° C./0.5 mm Hg.

REFERENCE EXAMPLE 34

A mixture of 4-methylphenol (54 g) and 4-chlorobutyryl chloride (77.5 g) was dissolved in xylene (250 ml). The mixture was heated gently until, at about 130° C., a vigorous reaction occurred. After the reaction had subsided, the mixture was heated at reflux for approximately 40 minutes, until the evolution of hydrogen chloride had ceased. The xylene was then removed in vacuo, and the residue was distilled to give 4-methylphenyl 4-chlorobutyrate (101 g), b.p. 116°–118° C./0.2 mm Hg.

REFERENCE EXAMPLE 35

Stirred aqueous sodium hydroxide solution (50% w/v; 90 ml) at 110° C. was treated with 2-hydroxy-5-methyl-(4-chlorobutyrophenone) (13.4 g) during a period of 20 minutes, during which the temperature of the reaction mixture was raised to 140° C. A further quantity of aqueous sodium hydroxide solution (50% w/v; 45 ml) was added, and the stirred mixture was heated at 140° C. for a further period of 2 hours. The mixture was then cooled, diluted with water (450 ml), acidified by treatment with glacial acetic acid, and steam distilled to give a yellow oil which was extracted with diethyl ether (3×100 ml). The ethereal extract was evaporated in vacuo and the resulting residue (6.43 g) crystallised on scratching. Recrystallisation from petroleum ether (b.p. 60°–80° C.) gave cyclopropyl 2-hydroxy-5-methylphenyl ketone, m.p. 66°–68° C.

REFERENCE EXAMPLE 36

A mixture of 4-bromo-2-methoxy-6-nitrophenol (7.0 g), anhydrous potassium carbonate (2.12 g) and benzyl chloride (3.93 g) in dry sulpholane (70 ml) was stirred at 90°–95° C. for 24 hours. The mixture was then diluted with water (300 ml) and the resulting oil was extracted with diethyl ether (3×50 ml). The combined ethereal extracts were washed with aqueous sodium carbonate solution (2 N; 2×50 ml) and then with water (3×20 ml), dried over anhydrous sodium sulphate and evaporated in vacuo to give a solid, which was recrystallised from ethanol to give 2-benzyloxy-5-bromo-3-methoxynitrobenzene (7.7 g), m.p. 74°–76° C.

By proceeding in a similar manner, but replacing the 4-bromo-2-methoxy-6-nitrophenol used as a starting material by the appropriate quantities of 2-methoxy-4-methyl-6-nitrophenol; and
4-ethyl-2-methoxy-6-nitrophenol; respectively, there were prepared
2-benzyloxy-3-methoxy-5-methylnitrobenzene, b.p. 173°–175° C./0.4 mm Hg; and
2-benzyloxy-5-ethyl-3-methoxynitrobenzene, b.p. 184°–186° C./0.1 mm Hg.

REFERENCE EXAMPLE 37

2-Hydroxy-5-methyl-3-nitrobenzoic acid (10.0 g) was dissolved in absolute ethanol (50 ml) and the solution was treated with concentrated sulphuric acid (3.0 ml), slowly with stirring. The mixture was heated at reflux for 20 hours and then poured into water (250 ml). The resulting yellow solid was recrystallised from ethanol to give ethyl 2-hydroxy-5-methyl-3-nitrobenzoate (7.5 g), m.p. 97° C.

By proceeding in a similar manner, but replacing the ethanol by anhydrous methanol, there was prepared methyl 2-hydroxy-5-methyl-3-nitrobenzoate, m.p. 145°–147° C. (recrystallised from methanol).

REFERENCE EXAMPLE 38

Methyl 2-hydroxy-5-methyl-3-nitrobenzoate (5.0 g) was dissolved in a solution of dimethylamine in ethanol (33% w/v; 50 ml) and the solution was heated at 100° C. in a sealed pressure vessel for 20 hours. The solvent was removed in vacuo and the residue was triturated with hydrochloric acid (2 N; 50 ml), and washed with water. Recrystallisation from methanol gave N,N-dimethyl-2-hydroxy-5-methyl-3-nitrobenzamide (3.0 g), m.p. 160°–162° C.

REFERENCE EXAMPLE 39

By proceeding as hereinbefore described in Reference Example 3 but replacing the oxalyl chloride, used as a starting material, by the appropriate quantity of thionyl chloride, there was prepared 1-benzyl-1H-tetrazole-5-carbonyl chloride.

REFERENCE EXAMPLE 40

By proceeding as hereinbefore described in Reference Example 3, but replacing the potassium 1-benzyl-1H-tetrazole-5-carboxylate used as a starting material by the appropriate quantity of potassium 2-benzyl-2H-tetrazole-5-carboxylate, there was prepared 2-benzyl-2H-tetrazole-5-carbonyl chloride.

REFERENCE EXAMPLE 41

A stirred, cooled suspension of potassium 1-(4-methoxybenzyl)-1H-tetrazole-5-carboxylate (0.82 g) in dry dimethylformamide (20 ml) was treated with N,N-dimethyl(chloromethyleneimmonium) chloride (0.39 g) and the mixture was stirred for 30 minutes. 3-Amino-5-ethyl-2-hydroxyacetophenone (0.54 g) was added, and the mixture was stirred for 20 hours at room temperature. The mixture was treated with dichloromethane (50 ml) and aqueous sodium carbonate solution (2 N; 15 ml), the organic layer was separated, washed with water (25 ml), dried over magnesium sulphate and evaporated, and the resulting residue was crystallised from acetic acid to give 3'-acetyl-5'-ethyl-2'-hydroxy-1-(4-methoxybenzyl)-1H-tetrazole-5-carboxanilide (0.2 g), m.p. 138°–139° C.

The present invention includes within its scope pharmaceutical compositions which comprise one or more compounds of formula I together with a pharmaceutical carrier or coating. In clinical practice the compounds of the present invention will normally be administered orally, sub-lingually, nasally, rectally, parenterally or topically.

Solid compositions for oral administration include compressed tablets, pills, dispersible powders, and granules. In such solid compositions the active compound or compounds is or are mixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing the active compound or compounds with or without the addition of diluents or excipients.

The compound(s) may also be administered sub-lingually by administration of relatively slowly dissolving tablets which, besides including inert diluents as commonly used in the art, may contain sweetening, flavouring, perfuming and preserving agents.

Solid compositions for rectal administration include suppositories formulated in manner known per se and containing the active compound or compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. Generally the compositions should contain 0.1% to 50% by weight of tetrazole derivative, especially when in tablet form. When in aerosol form as hereinafter described the compositions should contain 0.2 to 5%, preferably 2 to 5%, by weight of tetrazole derivative.

The active compound or compounds may also be administered by methods known for the inhalation of drugs which are not themselves gaseous under normal conditions of administration. Thus, a solution of the compound or compounds in a suitable pharmaceutically acceptable solvent, for example water, can be nebulized by a mechanical nebulizer, for example a Wright Nebulizer, to give an aerosol of finely-divided liquid particles suitable for administration for inhalation orally or nasally. The solutions may contain stabilizing agents and buffering agents to give an isotonic character, e.g. sodium chloride, sodium citrate and citric acid.

Means for producing self-propelling compositions for generating aerosols for the administration of medicaments are, for example, described in detail in U.S. Pat. Nos. 2,868,691 and 3,095,355.

The compound or compounds may also be administered orally by inhalation in the form of a dry micronised powder, which may be diluted with one or more suitable pharmaceutically acceptable inert solid diluents selected from, for example, lycopodium, boric acid, starch, bismuth subcarbonate and heavy magnesium carbonate.

The pharmaceutical compositions of the present invention may contain, in addition to the compound or compounds of formula I, one or more substances known per se to have bronchodilating actions in man, for example, isoprenaline, salbutamol and prostaglandin $E_1$ (PGE$_1$).

It is highly desirable that the aerosols or micronised powders should have a particle size less than about 10 microns and preferably less than 5 microns, for example, between 0.5 and 3 microns, to ensure effective distribution to very narrow bronchioles. Preferably, administration is by means of devices enabling controlled quantities of the active ingredients to be administered, for example by means of metered valves.

The dose of the compounds of general formula I employed depends upon the desired therapeutic effect, the route of administration and the duration of the treatment. In the adult, the doses are generally between 0.002 and 4, preferably between 0.002 and 0.4, mg/kg body weight per day by administration by inhalation in divided doses, and generally between 0.4 and 2000, preferably between 0.4 and 40, mg/kg body weight per day by oral administration.

The following Composition Examples illustrate pharmaceutical compositions according to the present invention:

COMPOSITION EXAMPLE 1

Micromilled 3'-acetyl-2'-hydroxy-5'-methyltetrazole-5-carboxanilide (600 mg) and emulsifier YN (150 mg; a mixture of ammonium compounds of phosphatidic acids derived from rape seed oil) were placed in an aluminium vial (20 ml capacity). Trichloromonofluoromethane (2.7 g), dichlorodifluoromethane (9.4 g) and dichlorotetrafluoroethane (4.4 g) were then added, to give a total volume of 12.5 ml. The vial was sealed with a metered valve delivering a dose of 0.05 ml. Each dose (generated from 0.05 ml of suspension) of aerosol released from the pressurised pack thus obtained contained 2.4 mg of 3'-acetyl-2'-hydroxy-5'-methyltetrazole-5-carboxanilide.

COMPOSITION EXAMPLE 2

Capsules for oral administration were made up in the usual manner by filling No. 2 size gelatin capsules each with 255 mg of the following composition:

| | |
|---|---|
| 3'-acetyl-2'-hydroxy-5'-methyltetrazole-5-carboxanilide | 150 mg |
| lactose | 50 mg |
| starch | 50 mg |
| magnesium stearate | 2.5 mg |
| aerosil | 2.5 mg. |

We claim:
1. A tetrazole of the formula:

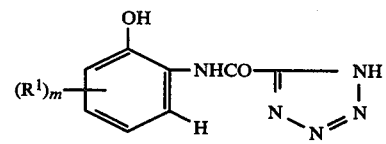

wherein $R^1$ represents a halogen atom, an alkyl, alkoxy, alkylthio, alkylsulphinyl, alkylsulphonyl or alkylsulphamoyl group, each such group having from 1 to 6 carbon atoms, a dialkylsulphamoyl, dialkylamino, or dialkylcarbamoyl group (wherein each of the two alkyl groups has from 1 to 4 carbon atoms), an alkanoyl, alkoxycarbonyl, alkoxycarbonylamino, alkylcarbamoyl or alkanoylamino group of from 2 to 6 carbon atoms, a cycloalkylcarbonyl group of from 3 to 8 carbon atoms in the cycloalkyl moiety, or a hydroxy, formyl, nitro, trifluoromethyl, trifluoroacetyl, phenyl, benzyloxycarbonylamino, amino, sulphamoyl, cyano, tetrazol-5-yl, carboxy, carbamoyl, benzyloxy, phenylacetyl or benzoyl group, or a group of the formula:

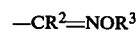
$-CR^2=NOR^3$

II (wherein $R^2$ represents a hydrogen atom, an alkyl group of from 1 to 5 carbon atoms, a phenyl, phenylalkyl or trifluoromethyl group, or a cycloalkyl group of 3 to 8 carbon atoms, and $R^3$ represents a hydrogen atom, an alkyl group of from 1 to 6 carbon atoms unsubstituted or substituted by a phenyl group, or represents a phenyl group unsubstituted or substituted by one substituent selected from halogen atoms and alkyl and alkoxy groups of from 1 to 6 carbon atoms and hydroxy, trifluoromethyl and nitro groups), and m represents zero, 1, or 2, the substituent $R^1$ being in the 3- or 5-position when m is 1 and the substituents $R^1$ being the same or different and being in the 3- and 5-positions when m is 2 and pharmaceutically acceptable salts thereof.

2. A tetrazole according to claim 1 wherein $R^1$ represents a halogen atom, an alkyl, alkoxy, alkylthio, alkylsulphonyl or alkylsulphamoyl group, each such group having from 1 to 6 carbon atoms, a dialkylsulphamoyl, dialkylamino, or dialkylcarbamoyl group (wherein each of the two alkyl groups has from 1 to 4 carbon atoms), an alkanoyl, alkoxycarbonyl, alkoxycarbonylamino, alkylcarbamoyl or alkanoylamino group of from 2 to 6 carbon atoms, or a hydroxy, formyl, nitro, trifluoromethyl, phenyl, benzyloxycarbonylamino, amino, sulphamoyl, cyano, tetrazol-5-yl, carboxy, carbamoyl, benzyloxy or benzoyl group, and m represents zero 1 or 2, the substituent $R^1$ being in the 3- or 5-position when m is 1 and the substituents $R^1$ being the same or different and being in the 3- and 5-positions when m is 2, and pharmaceutically acceptable salts thereof.

3. A tetrazole according to claim 1 wherein $R^1$ represents a halogen atom, an alkyl, alkoxy, or alkylsulphonyl group, each such group having from 1 to 4 carbon atoms, a dialkylcarbamoyl group (wherein each of the two alkyl groups has 1 or 2 carbon atoms), an alkanoyl, alkoxycarbonyl or alkanoylamino group of from 2 to 4 carbon atoms, a cycloalkylcarbonyl group of from 3 to 6 carbon atoms in the cycloalkyl moiety, or a nitro, trifluoroacetyl, amino, cyano, or phenylacetyl group, or a group of formula II depicted in claim 44 (wherein $R^2$ represents an alkyl group of from 1 to 3 carbon atoms, and $R^3$ represents a hydrogen atom or an alkyl group of from 1 to 3 carbon atoms), and m represents zero, 1 or 2, the substituent $R^1$ being in the 3- or 5-position when m represents 1 and the substituents $R^1$ being the same or different and being in the 3- and 5-positions when m is 2, and pharmaceutically acceptable salts thereof.

4. A tetrazole according to claim 1 wherein $R^1$ represents a fluorine or bromine atom or a methyl, ethyl, propyl, methoxy, methylsulphonyl, dimethylcarbamoyl, acetyl, propionyl, butyryl, isobutyryl, methoxycarbonyl, ethoxycarbonyl, acetylamino, cyclopropylcarbonyl, nitro, trifluoroacetyl, amino, cyano, phenylacetyl, 1-(hydroxyimino)ethyl or 1-(methoxyiminoethyl) group, and m represents zero, 1 or 2, the substituent $R^1$ being in the 3- or 5-position when m represents 1 and the substituent $R^1$ being the same or different and being in the 3- and 5-positions when m represents 2, and pharmaceutically acceptable salts thereof.

5. A tetrazole according to claim 1 wherein the benzene ring of general formula I depicted in claim 1 carries one or two substituents $R^1$ and one substituent $R^1$ represents an alkoxy group of from 1 to 4 carbon atoms or an alkanoyl or alkoxycarbonyl group of from 2 to 4 carbon atoms, or a group of formula II depicted in claim 1 (wherein $R^2$ and $R^3$ are as defined in claim 1), the other substituent $R^1$ if any present on the benzene ring being as defined in claim 44, and pharmaceutically acceptable salts thereof.

6. A tetrazole according to claim 1 wherein the benzene ring of general formula I depicted in claim 1 carries one or two substituents $R^1$ and one substituent $R^1$ represents an alkanoyl group of from 2 to 4 carbon atoms, the other substituent $R^1$ if any present on the benzene ring being as defined in claim 1, and pharmaceutically acceptable salts thereof.

7. A tetrazole according to claim 5 or 6 in which said substituent $R^1$ is in the 3-position of the benzene ring.

8. A tetrazole according to claim 1 which is 2'-hydroxytetrazole-5-carboxanilide.

9. A tetrazole according to claim 1 which is 3'-acetyl-2'-hydroxy-5'-methyltetrazole-5-carboxanilide.

10. A tetrazole according to claim 1 which is 3'-ethyl-2'-hydroxytetrazole-5-carboxanilide.

11. A tetrazole according to claim 1 which is 3'-acetyl-5'-ethyl-2'-hydroxytetrazole-5-carboxanilide.

12. A tetrazole according to claim 1 which is 3'-acetyl-2'-hydroxy-5'-nitrotetrazole-5-carboxanilide.

13. A tetrazole according to claim 1 which is 3'-acetyl-5'-acetylamino-2'-hydroxytetrazole-5-carboxanilide.

14. A tetrazole according to claim 1 which is 2'-hydroxy-3'-isobutyryl-5'-methyltetrazole-5-carboxanilide.

15. A tetrazole according to claim 1 which is 3'-acetyl-5'-cyano-2'-hydroxytetrazole-5-carboxanilide.

16. A tetrazole according to claim 1 which is 3'-cyclopropylcarbonyl-2'-hydroxy-5'-methyltetrazole-5-carboxanilide.

17. A tetrazole according to claim 1 which is 2'-hydroxy-5'-methyl-3'-trifluoroacetyltetrazole-5-carboxanilide.

18. A tetrazole according to claim 1 which is 3'-acetyl-5'-fluoro-2'-hydroxytetrazole-5-carboxanilide.

19. A tetrazole according to claim 1 which is 3'-acetyl-5'-bromo-2'-hydroxytetrazole-5-carboxanilide.

20. A tetrazole according to claim 1 which is 3'-acetyl-2'-hydroxy-5'-methoxytetrazole-5-carboxanilide.

21. A tetrazole according to claim 1 which is 5'-cyano-2'-hydroxy-3'-propionyltetrazole-5-carboxanilide.

22. A tetrazole according to claim 1 which is 2'-hydroxy-5'-methyl-3'-phenylacetyl-tetrazole-5-carboxanilide.

23. A tetrazole according to claim 1 which is 3'-acetyl-5'-amino-2'-hydroxytetrazole-5-carboxanilide.

24. A tetrazole according to claim 1 which is 3'-acetyl-2'-hydroxy-5'-methylsulphonyltetrazole-5-carboxanilide.

25. A tetrazole according to claim 1 which is 2'-hydroxy-3'-methoxytetrazole-5-carboxanilide.

26. A tetrazole according to claim 1 which is 5'-ethyl-2'-hydroxy-3'-methoxytetrazole-5-carboxanilide.

27. A tetrazole according to claim 1 which is 2'-hydroxy-3'-methoxy-5'-methyltetrazole-5-carboxanilide.

28. A tetrazole according to claim 1 which is 3'-butyryl-2'-hydroxy-5'-methyltetrazole-5-carboxanilide.

29. A tetrazole according to claim 1 which is 3'-(N,N-dimethylcarbamoyl)-2'-hydroxy-5'-methyltetrazole-5-carboxanilide.

30. A tetrazole according to claim 1 which is 2'-hydroxy-3'-methoxycarbonyl-5'-methyltetrazole-5-carboxanilide.

31. A tetrazole according to claim 1 which is 3'-ethoxycarbonyl-2'-hydroxy-5'-methyltetrazole-5-carboxanilide.

32. A tetrazole according to claim 1 which is 3'-acetyl-2'-hydroxy-5'-propyltetrazole-5-carboxanilide.

33. A tetrazole according to claim 1 which is 3'-acetyl-2'-hydroxytetrazole-5-carboxanilide.

34. A tetrazole according to claim 1 which is 5'-ethyl-2'-hydroxy-3'-propionyltetrazole-5-carboxanilide.

35. A tetrazole according to claim 1 which is 2'-hydroxy-5'-methyl-3'-propionyltetrazole-5-carboxanilide.

36. A tetrazole according to claim 1 which is 5'-bromo-2'-hydroxy-3'-methoxytetrazole-5-carboxanilide.

37. A tetrazole according to claim 1 which is 2'-hydroxy-3'-(1-hydroxyimino)ethyl-5'-methyltetrazole-5-carboxanilide.

38. A tetrazole according to claim 1 which is 2'-hydroxy-3'-(1-methoxyimino)ethyl-5'-methyltetrazole-5-carboxanilide.

39. A tetrazole according to claim 1 which is 5'-ethyl-2'-hydroxy-3'-(1-hydroxyimino)ethyltetrazole-5-carboxanilide.

40. A tetrazole according to claim 1 which is 5'-ethyl-2'-hydroxy-3'-(1-methoxyimino)ethyltetrazole-5-carboxanilide.

41. A pharmaceutically acceptable salt of a compound as claimed in 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40.

42. A pharmaceutical composition useful in the treatment of allergic conditions which comprises, as active ingredient, an effective amount of a tetrazole as claimed in claim 1, or a pharmaceutically acceptable salt thereof, in association with a pharmaceutical carrier.

43. A composition according to claim 42 in which the active ingredient is 3'-acetyl-5'-fluoro-2'-hydroxytetrazole-5-carboxanilide.

* * * * *